United States Patent [19]

Fronticelli et al.

[11] Patent Number: 5,239,061
[45] Date of Patent: Aug. 24, 1993

[54] MODIFIED HUMAN HEMOGLOBIN, BLOOD SUBSTITUTES CONTAINING THE SAME, AND VECTORS FOR EXPRESSING THE MODIFIED HEMOGLOBIN

[75] Inventors: Clara Fronticelli; Enrico Bucci, both of Baltimore, Md.; William Brinigar, Strafford, Pa.

[73] Assignee: Research Corporation Technologies, Inc., Tucson, Ariz.

[21] Appl. No.: 541,011

[22] Filed: Jun. 20, 1990

[51] Int. Cl.$^5$ .................... A61K 35/14; C07K 13/00
[52] U.S. Cl. .................. 530/385; 530/387.3
[58] Field of Search .............. 530/385, 387.3; 424/78

[56] References Cited

FOREIGN PATENT DOCUMENTS 8809179 12/1988 European Pat. Off. .

OTHER PUBLICATIONS

Bonoventura et al J of Biol Chem 250:6273-6277 1975 (1).
Luisi et al Nature 320:555-556 1986.
Nagai et al PNAS 82:7252-7255 1985 (1).
Nagai et al (2) Nature 329:858-860 1987.
Bonoventura et al J of Biol Chem 243:980-991 1968 (2).
Razynska et al, Biophysical Chemistry, vol. 38, pp. 111-115.
Fronticelli, Biophysical Chemistry, vol. 37, pp. 141-146.
Fronticelli et al, J. Mol. Biol., vol. 202, pp. 343-348 (1988).

Primary Examiner—Christine M. Nucker
Assistant Examiner—H. F. Sidberry
Attorney, Agent, or Firm—Birch, Stewart, Kolasch & Birch

[57] ABSTRACT

The present invention relates to modified $\beta$-chains of human hemoglobin having an oxygen binding affinity equal to or less than natural human hemoglobin. The modified the $\beta$-chain of human hemoglobin of the invention preferably has at least one chloride binding site not present in $\beta$-chain of natural human hemoglobin.

5 Claims, 13 Drawing Sheets

Histogram of the hydrophobicity values calculated for the regions βNA1-A7 (top) and βE8-EF5 (bottom) of the β-chains of the primate and ruminant hemoglobins listed in table I.

FIG. 6
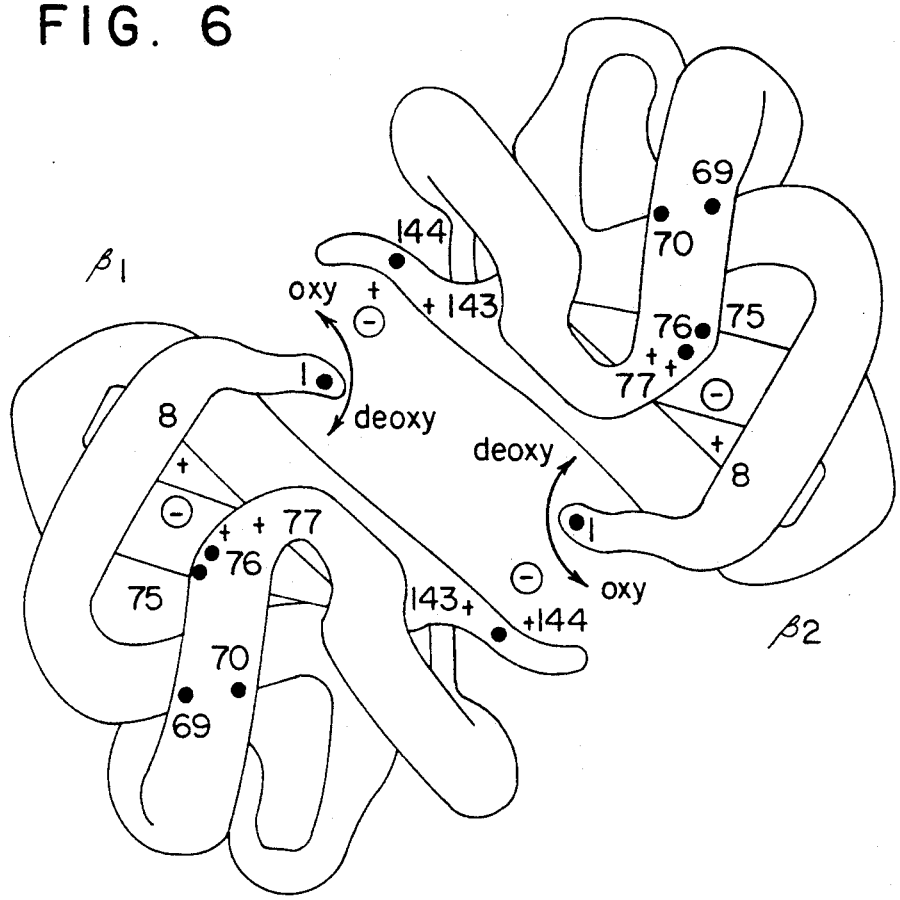
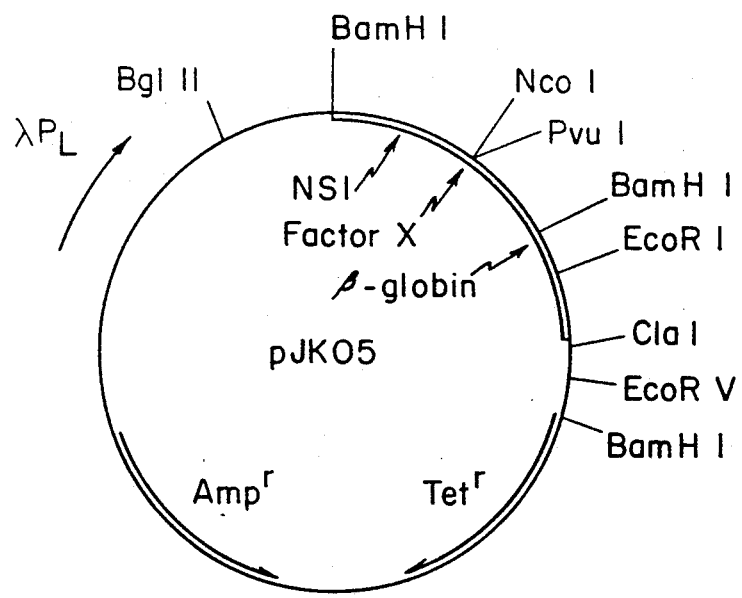
FIG. 7

```
     ATGGATCCAAACACTGTGTCAAGCTTTCAGGTAGATTGCTTTCTTTGGCATGTCCGCAAA
1850 +---------+---------+---------+---------+---------+---------- 1909
     TACCTAGGTTTGTGACACAGTTCGAAAGTCCATCTAACGAAAGAAACCGTACAGGCGTTT

MetAspProAsnThrValSerSerPheGlnValAspCysPheLeuTrpHisValArgLys -

CGAGTTGCAGACCAAGAACTAGGTGATGCCCCATTCCTTGATCGGCTTCGCCGAGATCAG
1910 +---------+---------+---------+---------+---------+---------- 1969
     GCTCAACGTCTGGTTCTTGATCCACTACGGGGTAAGGAACTAGCCGAAGCGGCTCTAGTC

ArgValAlaAspGlnGluLeuGlyAspAlaProPheLeuAspArgLeuArgArgAspGln -

AAATCCCTAAGAGGAAGGGGCAGCACTCTTGGTCTGGACATCGAGACAGCCACACGTGCT
1970 +---------+---------+---------+---------+---------+---------- 2029
     TTTAGGGATTCTCCTTCCCCGTCGTGAGAACCAGACCTGTAGCTCTGTCGGTGTGCACGA

LysSerLeuArgGlyArgGlySerThrLeuGlyLeuAspIleGluThrAlaThrArgAla -

GGAAAGCAGATAGTGGAGCGGATTCTGAAAGAAGAATCCGATGAGGCACTTAAAATGACC
2030 +---------+---------+---------+---------+---------+---------- 2089
     CCTTTCGTCTATCACCTCGCCTAAGACTTTCTTCTTAGGCTACTCCGTGAATTTTACTGG

GlyLysGlnIleValGluArgIleLeuLysGluGluSerAspGluAlaLeuLysMetThr -
                                                     CGA
     ATGGCGATCGAGGGTAGGGTGCACCTGACTCCTGAGGAGAAGTCTGCGGTTACTGCCCTG
2090 +---------+---------+---------+---------+---------+---------- 2149
     TACCGCTAGCTCCCATCCCACGTGGACTGAGGACTCCTCTTCAGACGCCAATGACGGGAC
                                                     GCT
     MetAlaIleGluGlyArgValHisLeuThrProGluGluLysSerAlaValThrAlaLeu -
           FX           Asp  5                  10
     TGGGGCAAGGTGAACGTGGATGAAGTTGGTGGTGAGGCCCTGGGCAGGCTGCTGGTGGTC
2150 +---------+---------+---------+---------+---------+---------- 2209
     ACCCCGTTCCACTTGCACCTACTTCAACCACCACTCCGGGACCCGTCCGACGACCACCAG

TrpGlyLysValAsnValAspGluValGlyGlyGluAlaLeuGlyArgLeuLeuValVal -
       15           20          25           30
     TACCCTTGGACCCAGAGGTTCTTTGAGTCCTTTGGGGATCTGTCCACTCCTGATGCAGTT
2210 +---------+---------+---------+---------+---------+---------- 2269
     ATGGGAACCTGGGTCTCCAAGAAACTCAGGAAACCCCTAGACAGGTGAGGACTACGTCAA

TyrProTrpThrGlnArgPhePheGluSerPheGlyAspLeuSerThrProAspAlaVal -
         35           40          45          50
     ATGGGCAACCCTAAGGTGAAGGCTCATGGCAAGAAAGTGCTCGGTGCCTTTAGTGATGGC
2270 +---------+---------+---------+---------+---------+---------- 2329
     TACCCGTTGGGATTCCACTTCCGAGTACCGTTCTTTCACGAGCCACGGAAATCACTACCG

MetGlyAsnProLysValLysAlaHisGlyLysLysValLeuGlyAlaPheSerAspGly -
         55           60          65          70
     CTGGCTCACCTGGACAACCTCAAGGGCACCTTTGCCACACTGAGTGAGCTGCACTGTGAC
2330 +---------+---------+---------+---------+---------+---------- 2389
     GACCGAGTGGACCTGTTGGAGTTCCCGTGGAAACGGTGTGACTCACTCGACGTGACACTG

LeuAlaHisLeuAspAsnLeuLysGlyThrPheAlaThrLeuSerGluLeuHisCysAsp -
         75           80          85          90
     AAGCTGCACGTGGATCCTGAGAACTTCAGGCTCCTGGGCAACGTGCTGGTCTGTGTGCTG
2390 +---------+---------+---------+---------+---------+---------- 2449
     TTCGACGTGCACCTAGGACTCTTGAAGTCCGAGGACCCGTTGCACGACCAGACACACGAC
```

FIG. 13A

```
          LysLeuHisValAspProGluAsnPheArgLeuLeuGlyAsnValLeuValCysValLeu -
              95           100          105          110
          GCCCATCACTTTGGCAAAGAATTCACCCCACCAGTGCAGGCTGCCTATCAGAAAGTGGTG
     2450 +---------+---------+---------+---------+---------+---------  2509
          CGGGTAGTGAAACCGTTTCTTAAGTGGGGTGGTCACGTCCGACGGATAGTCTTTCACCAC

AlaHisHisPheGlyLysGluPheThrProProValGlnAlaAlaTyrGlnLysValVal -
              115          120          125          130
          GCTGGTGTGGCTAATGCCCTGGCCCACAAGTATCACTAA
     2510 +---------+---------+---------+--------  2548
          CGACCACACCGATTACGGGACCGGGTGTTCATAGTGATT

AlaGlyValAlaAsnAlaLeuAlaHisLysTyrHisEnd -
              135          140          145
```

FIG. 13B

```
      ATGGATCCAAACACTGTGTCAAGCTTTCAGGTAGATTGCTTTCTTTGGCATGTCCGCAAA
1850  +---------+---------+---------+---------+---------+---------  1909
      TACCTAGGTTTGTGACACAGTTCGAAAGTCCATCTAACGAAAGAAACCGTACAGGCGTTT
           NS1  -  -  -  -  -
      MetAspProAsnThrValSerSerPheGlnValAspCysPheLeuTrpHisValArgLys -

CGAGTTGCAGACCAAGAACTAGGTGATGCCCCATTCCTTGATCGGCTTCGCCGAGATCAG
1910  +---------+---------+---------+---------+---------+---------  1969
      GCTCAACGTCTGGTTCTTGATCCACTACGGGGTAAGGAACTAGCCGAAGCGGCTCTAGTC

ArgValAlaAspGlnGluLeuGlyAspAlaProPheLeuAspArgLeuArgArgAspGln -

AAATCCCTAAGAGGAAGGGGCAGCACTCTTGGTCTGGACATCGAGACAGCCACACGTGCT
1970  +---------+---------+---------+---------+---------+---------  2029
      TTTAGGGATTCTCCTTCCCCGTCGTGAGAACCAGACCTGTAGCTCTGTCGGTGTGCACGA

LysSerLeuArgGlyArgGlySerThrLeuGlyLeuAspIleGluThrAlaThrArgAla -

GGAAAGCAGATAGTGGAGCGGATTCTGAAAGAAGAATCCGATGAGGCACTTAAAATGACC
2030  +---------+---------+---------+---------+---------+---------  2089
      CCTTTCGTCTATCACCTCGCCTAAGACTTTCTTCTTAGGCTACTCCGTGAATTTTACTGG

GlyLysGlnIleValGluArgIleLeuLysGluGluSerAspGluAlaLeuLysMetThr -
           A   C TA del       G
      ATGGCGATCGAGGGTAGGGTGCACCTGACTCCTGAGGAGAAGTCTGCGGTTACTGCCCTG
2090  +---------+---------+---------+---------+---------+---------  2149
      TACCGCTAGCTCCCATCCCACGTGGACTGAGGACTCCTCTTCAGACGCCAATGACGGGAC
            T   G AT del        C
      MetAlaIleGluGlyArgValHisLeuThrProGluGluLysSerAlaValThrAlaLeu -
           FX           Met —— β-Globin - - -
      TGGGGCAAGGTGAACGTGGATGAAGTTGGTGGTGAGGCCCTGGGCAGGCTGCTGGTGGTC
2150  +---------+---------+---------+---------+---------+---------  2209
      ACCCCGTTCCACTTGCACCTACTTCAACCACCACTCCGGGACCCGTCCGACGACCACCAG TrpGlyLysValAsnValAspGluValGlyGlyGluAlaLeuGlyArgLeuLeuValVal -

TACCCTTGGACCCAGAGGTTCTTTGAGTCCTTTGGGGATCTGTCCACTCCTGATGCAGTT
2210  +---------+---------+---------+---------+---------+---------  2269
      ATGGGAACCTGGGTCTCCAAGAAACTCAGGAAACCCCTAGACAGGTGAGGACTACGTCAA

TyrProTrpThrGlnArgPhePheGluSerPheGlyAspLeuSerThrProAspAlaVal -

ATGGGCAACCCTAAGGTGAAGGCTCATGGCAAGAAAGTGCTCGGTGCCTTTAGTGATGGC
2270  +---------+---------+---------+---------+---------+---------  2329
      TACCCGTTGGGATTCCACTTCCGAGTACCGTTCTTTCACGAGCCACGGAAATCACTACCG

MetGlyAsnProLysValLysAlaHisGlyLysLysValLeuGlyAlaPheSerAspGly -

CTGGCTCACCTGGACAACCTCAAGGGCACCTTTGCCACACTGAGTGAGCTGCACTGTGAC
2330  +---------+---------+---------+---------+---------+---------  2389
      GACCGAGTGGACCTGTTGGAGTTCCCGTGGAAACGGTGTGACTCACTCGACGTGACACTG

LeuAlaHisLeuAspAsnLeuLysGlyThrPheAlaThrLeuSerGluLeuHisCysAsp -

AAGCTGCACGTGGATCCTGAGAACTTCAGGCTCCTGGGCAACGTGCTGGTCTGTGTGCTG
2390  +---------+---------+---------+---------+---------+---------  2449
      TTCGACGTGCACCTAGGACTCTTGAAGTCCGAGGACCCGTTGCACGACCAGACACACGAC
```

FIG. 14A

```
              LysLeuHisValAspProGluAsnPheArgLeuLeuGlyAsnValLeuValCysValLeu -

GCCCATCACTTTGGCAAAGAATTCACCCCACCAGTGCAGGCTGCCTATCAGAAAGTGGTG
      2450    +---------+---------+---------+---------+---------+---------  2509
              CGGGTAGTGAAACCGTTTCTTAAGTGGGGTGGTCACGTCCGACGGATAGTCTTTCACCAC

AlaHisHisPheGlyLysGluPheThrProProValGlnAlaAlaTyrGlnLysValVal -
                                                         CGT
              GCTGGTGTGGCTAATGCCCTGGCCCACAAGTATCACTAA
      2510    +---------+---------+---------+--------  2548
              CGACCACACCGATTACGGGACCGGGTGTTCATAGTGATT
                                                         GCA
              AlaGlyValAlaAsnAlaLeuAlaHisLysTyrHisEnd -
                                                         Arg
```

FIG. 14B

MODIFIED HUMAN HEMOGLOBIN, BLOOD SUBSTITUTES CONTAINING THE SAME, AND VECTORS FOR EXPRESSING THE MODIFIED HEMOGLOBIN This invention was made with Government support under Contract Nos. HL-13164 and HL-33629 awarded by the National Institutes of Health. The Government has certain rights in the invention.

BACKGROUND OF THE INVENTION

1. Field of the Invention

The present invention relates to modified human hemoglobins having an oxygen binding affinity equal or less than natural human hemoglobin, a blood product containing the same, and vectors containing a DNA sequence coding for the modified human hemoglobins.

2. Description of Related Art

In human red cells, the interaction of 2,3-DPG with hemoglobin (hemoglobin Hb) regulates the efficient release of oxygen to the tissues (R. Benesch et al, Nature, 221, 618 (1969)). Bovine red cells do not contain appreciable amounts of 2,3-DPG (H. F. Bunn, Science, 172, 1049 (1971)), however, human and bovine erythrocytes have the same oxygen affinity, indicating that either bovine Hb has an intrinsically low oxygen affinity, or that the oxygen affinity of this Hb becomes physiologically acceptable through a different mechanism of regulation.

The present inventors have observed that, in the absence of organic and inorganic anions, the oxygen affinities of human and bovine Hbs are similar (C. Fronticelli et al, J. Biol. Chem., 259, 10841 (1984)), indicating that the low oxygen affinity of bovine Hb could not be an intrinsic property of the molecule. Furthermore, the present inventors have found that bovine Hb has a particular sensitivity to chlorides and, as a result, at physiological chloride concentration (0.1 M) it could attain oxygen affinity values lower than those measured for human Hb in the presence of 2,3-DPG (C. Fronticelli et al, J. Mol. Biol., 202, 343 (1988)). The data indicated that the enhanced sensitivity of bovine Hb to the solvent components was due to the presence of extra chloride-binding sites, absent in human Hb. The inventors have also discovered that bovine Hb could discriminate between the halides on the basis of the charge density of the molecules (C. Fronticelli et al, J. Mol. Biol., 202, 343 (1988)), as if the interaction of the protein with the anions was modulated by the hydrophobic characteristics of the protein.

The different functional characteristics and the different number of Cl binding sites of human and bovine Hbs must originate from the amino acid compositions of the two proteins.

The sequence of natural $\beta$-chain of hemoglobin is as follows:

Natural $\beta$-Chain of Hemoglobin

```
Val His Leu Thr Pro Glu Glu Lys Ser Ala Val Thr Ala Leu Trp Gly Lys
             5                  10                     15

Val Asn Val Asp Glu Val Gly Gly Glu Ala Leu Gly Arg Leu Leu Val Val
         20                  25                  30

Tyr Pro Trp Thr Gln Arg Phe Phe Glu Ser Phe Gly Asp Leu Ser Thr Pro
 35                      40                  45                  50

Asp Ala Val Met Gly Asn Pro Lys Val Lys Ala His Gly Lys Lys Val Leu
             55                  60                  65

Gly Ala Phe Ser Asp Gly Leu Ala His Leu Asp Asn Leu Lys Gly Thr Phe
         70                  75                  80                  85

Ala Thr Leu Ser Glu Leu His Cys Asp Lys Leu His Val Asp Pro Glu Asn
                 90                  95                  100

Phe Arg Leu Leu Gly Asn Val Leu Val Cys Val Leu Ala His His Phe Gly
         105                  110                 115

Lys Glu Phe Thr Pro Pro Val Gln Ala Ala Tyr Gln Lys Val Val Ala Gly
 120                 125                 130                 135

Val Ala Asn Ala Leu Ala His Lys Tyr His End
         140                 145
```

Mutant hemoglobin molecules are disclosed in PCT Publication International Publication No. WO 88/09179 which was published on Dec. 1, 1988, which is hereby incorporated by reference.

SUMMARY OF THE INVENTION

The present invention relates to modified $\beta$-chains of human hemoglobin having an oxygen binding affinity equal to or less than natural human hemoglobin. Preferably, the oxygen binding affinity $P_{50}$ of the modified $\beta$-chains is in the range of about 3 to 70 mmHG as measured at temperatures in the range of about 10° to 40° C., at pH 7.4, in the presence of 0.1 to 0.2 M chloride. The modified the $\beta$-chain of human hemoglobin of the invention preferably has at least one chloride binding site not present in the $\beta$-chain of natural human hemoglobin. Also, the modified $\beta$-chain of human hemoglobin of the invention has additional negative charges at the N-terminal residues of the $\beta$-chains. Moreover, the modified $\beta$-chain of human hemoglobin of the invention may have hydrophobic residues, (e.g., Ala, Gly, Leu, Met, Phe, Pro, Ser, Thr, Trp, Tyr or Val) at the N-terminal residues of the $\beta$-chains. Representative examples of the modified $\beta$-chain of human hemoglobin include the following site specific mutants:

1) NA1 (1) Val→Met; delete NA2 (2) His.
2) HC1 (144) Lys→Arg.
3) NA1 (1) Val→Met; NA2 (2) His deleted; HC1 (144) Lys→Arg.

4) NA1(1) Val→Met; NA2 (2) His deleted; E20 (76)Ala→Lys.
5) NA1(1) Val→Met; NA2 (2) His deleted; E20 (76) Ala→Lys; HCl (144) Lys→Arg.
6) NA3 (3) Leu→Glu or Asp.
7) A1 (4) Thr→Glu or Asp.
8) A2 (5) Pro→Asp or Glu.
9) A2 (5) Pro→Gly, Ala or an amino acid having greater backbone flexibility.
10) E13 (69) Gly→Glu or Asp.
11) E14 (70) Ala→Thr or Ser.
12) E19 (75) Leu→Cyst or Met.

13) E20 (76) Ala→Arg, His, or Lys.
14) NA1 (1) Val→Met or Leu.

15) NA2 (2) His→Leu, Tyr or Asp.
16) NA1 (1) Val, NA2 (2) Hist→Met-Leu, Met-Asp, Met-Tyr, Leu-Leu, Leu-Asp or Leu-Tyr.

17) NA1 (1) Val→(Gly)$_n$ - Cys, where n is 1 to 20.
18) E11 (67) Val→Thr.

The number in the parenthesis in the above list of mutants represents the sequence number of the amino acids in the β-chains. For instance, in mutant (1) above, "NA1" represents the position of the amino acid at the N-terminal portion of the Hb crystal. The value "(1)", as mentioned above, represents the sequence number of the amino acid of interest. "→Met" means substitute the amino acid of interest with "Met".

The modified β-chain which has actually been expressed has the following amino acid sequence.

(1) Val ⟶ Met; (2) His deleted; (144) Lys ⟶ Arg

Met Leu Thr Pro Glu Glu Lys Ser Ala Val Thr Ala Leu Trp Gly Lys
           5             10             15

Val Asn Val Asp Glu Val Gly Gly Glu Ala Leu Gly Arg Leu Leu Val Val
         20           25          30

Tyr Pro Trp Thr Gln Arg Phe Phe Glu Ser Phe Gly Asp Leu Ser Thr Pro
35          40          45          50

Asp Ala Val Met Gly Asn Pro Lys Val Lys Ala His Gly Lys Lys Val Leu
        55          60          65

Gly Ala Phe Ser Asp Gly Leu Ala His Leu Asp Asn Leu Lys Gly Thr Phe
70          75          80

Ala Thr Leu Ser Glu Leu His Cys Asp Lys Leu His Val Asp Pro Glu Asn
85          90          95          100

Phe Arg Leu Leu Gly Asn Val Leu Val Cys Val Leu Ala His His Phe Gly
        105         110         115

Lys Glu Phe Thr Pro Pro Val Gln Ala Ala Tyr Gln Lys Val Val Ala Gly
120         125         130         135

Val Ala Asn Ala Leu Ala His Arg Tyr His End
140         145

Mutant A1 (4) Thr→Asp has the following sequence:

Val His Leu Asp Pro Glu Lys Ser Ala Val Thr Ala Leu Trp Gly Lys
         5          10          15

Val Asn Val Asp Glu Val Gly Gly Glu Ala Leu Gly Arg Leu Leu Val Val
        20          25          30

Tyr Pro Trp Thr Gln Arg Phe Phe Glu Ser Phe Gly Asp Leu Ser Thr Pro
35          40          45          50

Asp Ala Val Met Gly Asn Pro Lys Val Lys Ala His Gly Lys Lys Val Leu
        55          60          65

Gly Ala Phe Ser Asp Gly Leu Ala His Leu Asp Asn Leu Lys Gly Thr Phe
70          75          80          85

Ala Thr Leu Ser Glu Leu His Cys Asp Lys Leu His Val Asp Pro Glu Asn
        90          95          100

Phe Arg Leu Leu Gly Asn Val Leu Val Cys Val Leu Ala His His Phe Gly
        105         110         115

Lys Glu Phe Thr Pro Pro Val Gln Ala Ala Tyr Gln Lys Val Val Ala Gly
120         125         130         135

Val Ala Asn Ala Leu Ala His Lys Tyr His End
140         145

Mutant E11 (67) Val→Thr has the following sequence:

Val His Leu Thr Pro Glu Glu Lys Ser Ala Val Thr Ala Leu Trp Gly Lys
 5                          10                      15

Val Asn Val Asp Glu Val Gly Gly Glu Ala Leu Gly Arg Leu Leu Val Val
 20                  25                      30

Tyr Pro Trp Thr Gln Arg Phe Phe Glu Ser Phe Gly Asp Leu Ser Thr Pro
 35              40                  45                  50

Asp Ala Val Met Gly Asn Pro Lys Val Lys Ala His Gly Lys Lys Thr Leu
         55                      60                  65

Gly Ala Phe Ser Asp Gly Leu Ala His Leu Asp Asn Leu Lys Gly Thr Phe
 70              75                  80              85

Ala Thr Leu Ser Glu Leu His Cys Asp Lys Leu His Val Asp Pro Glu Asn
                 90                  95              100

Phe Arg Leu Leu Gly Asn Val Leu Val Cys Val Leu Ala His His Phe Gly
             105                 110             115

Lys Glu Phe Thr Pro Pro Val Gln Ala Ala Tyr Gln Lys Val Val Ala Gly
120                 125             130                 135

Val Ala Asn Ala Leu Ala His Lys Tyr His End
140                     145

The invention is further directed to modified human hemoglobin containing the above described modified β-chain and having enhanced sensitivity toward chloride, said hemoglobin having lower oxygen affinity than natural human hemoglobin, with and without cooperative oxygen binding.

the modified β-chain of human hemoglobin of the invention and which is capable of expressing the above-described modified β-chain of human hemoglobin. The mRNA transcript which corresponds to the cloned DNA sequence which has been used to express modified β-chain of human hemoglobin has the sequence:

```
                                          -15                    -10
                       m⁷GpppAC AUU UGC UUC UGA CAC AAC UGU GUU CAC
         -5                       0                       5
UAG CAA CCU CAA ACA GAC ACC AUG GUG CAC CUG ACU CCU GAG GAG AAG UCU
     10                  15                      20                      25
GCC GUU ACU GCC CUG UGG GGC AAG GUG AAC GUG GAU GAA GUU GGU GGU GAG
                 30                      35                  40
GCC CUG GGC AGG CUG CUG GUG GUC UAC CCU UGG ACC CAG AGG UUC UUU GAG
         45                      50                      55                  60
UCC UUU GGG GAU CUG UCC ACU CCU GAU GCU GUU AUG GGC AAC CCU AAG GUG
                     65                      70                      75
AAG GCU CAU GGC AAG AAA GUG CUC GGU GCC UUU AGU GAU GGC CUG GCU CAC
             80                      85                  90
CUG GAC AAC CUC AAG GGC ACC UUU GCC ACA CUG AGU GAG CUG CAC UGU GAC
 95                      100                     105                     110
AAG CUG CAC GUG GAU CCU GAG AAC UUC AGG CUC CUG GGC AAC GUG CUG GUC
                 115                     120                     125
UGU GUG CUG GCC CAU CAC UUU GGC AAA GAA UUC ACC CCA CCA GUG CAG GCU
             130                     135                     140             145
GCC UAU CAG AAA GUG GUG GCU GGU GUG GCU AAU GCC CUG GCC CAC AAG UAU
                         150                     155                 160
CAC UAA GCU CGC UUU CUU GCU GUC CAA UUU CUA UUA AAG GUU CCU UUG UUC
             165                     170                     175
CCU AAG UCC AAC UAC UAA ACU GGG GGA UAU UAU GAA GGG CCU UGA GCA UCU
         180                      185                 190
GGA UUC UGC CUA AUA AAA AAC AUU UAU UUU CAU UGC POLY A
```

The invention also prevents the disassociation of the modified human hemoglobin in α-β dimers, by introducing Cys-S-S-Cys crosslinks between the α-chains, the β-chains, or both the α and β-chains.

The invention further relates to DNA or a vector containing a DNA (e.g., cDNA) sequence coding for

BRIEF DESCRIPTION OF THE DRAWINGS

FIG. 6 shows the β-chains of human hemoglobin viewed down the two-fold symmetry axis.

FIG. 7 shows a plasmid encoding fusion proteins of the Nagai-Thogersen type. The plasmid contains human β-globin with a Factor X (FX) recognition sequence appended to the 5'-end of the globin gene. Upstream of the FX sequence is the N-terminal 81 residues of NS1, a flu virus protein. The amino acid sequence at the fusion junction is shown below the plasmid map.

Figure 1:
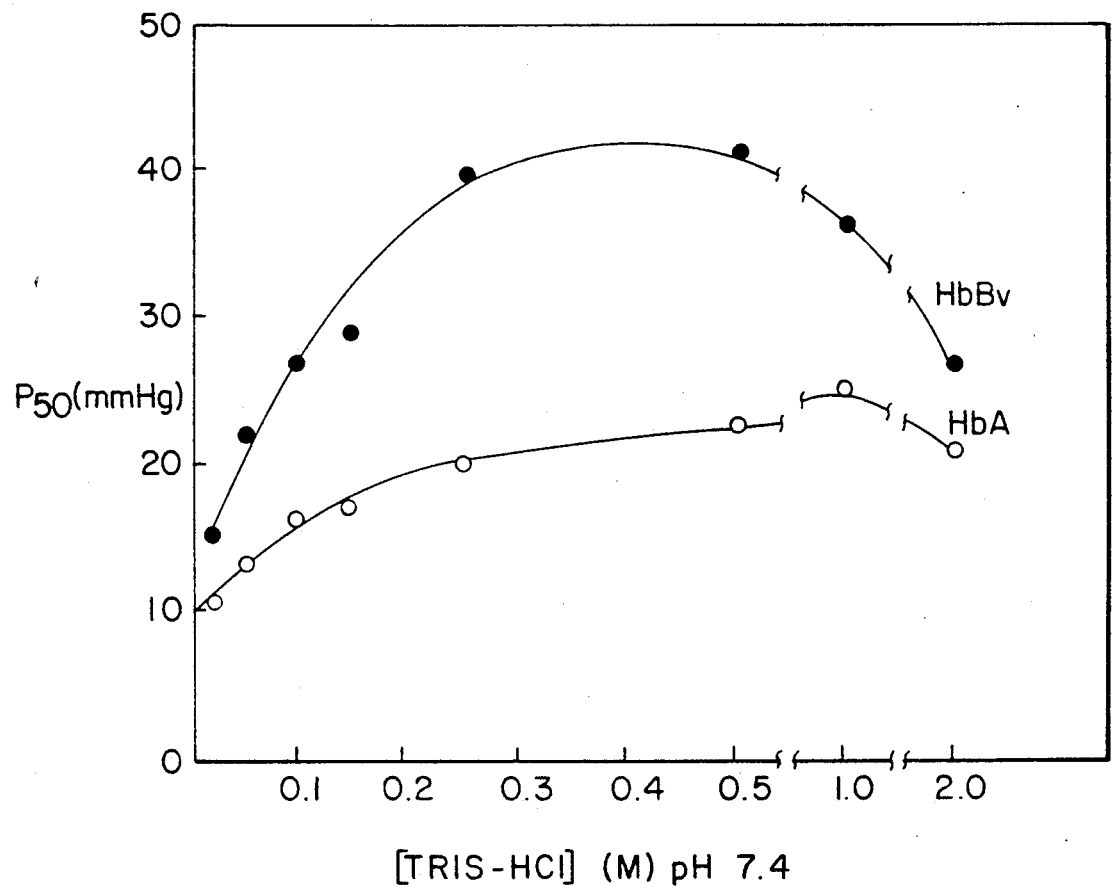
FIG. 1 shows the oxygen affinity of human (HbA) and bovine hemoglobin (HbBv) at increasing concentrations of chloride ions.
Figure 2:
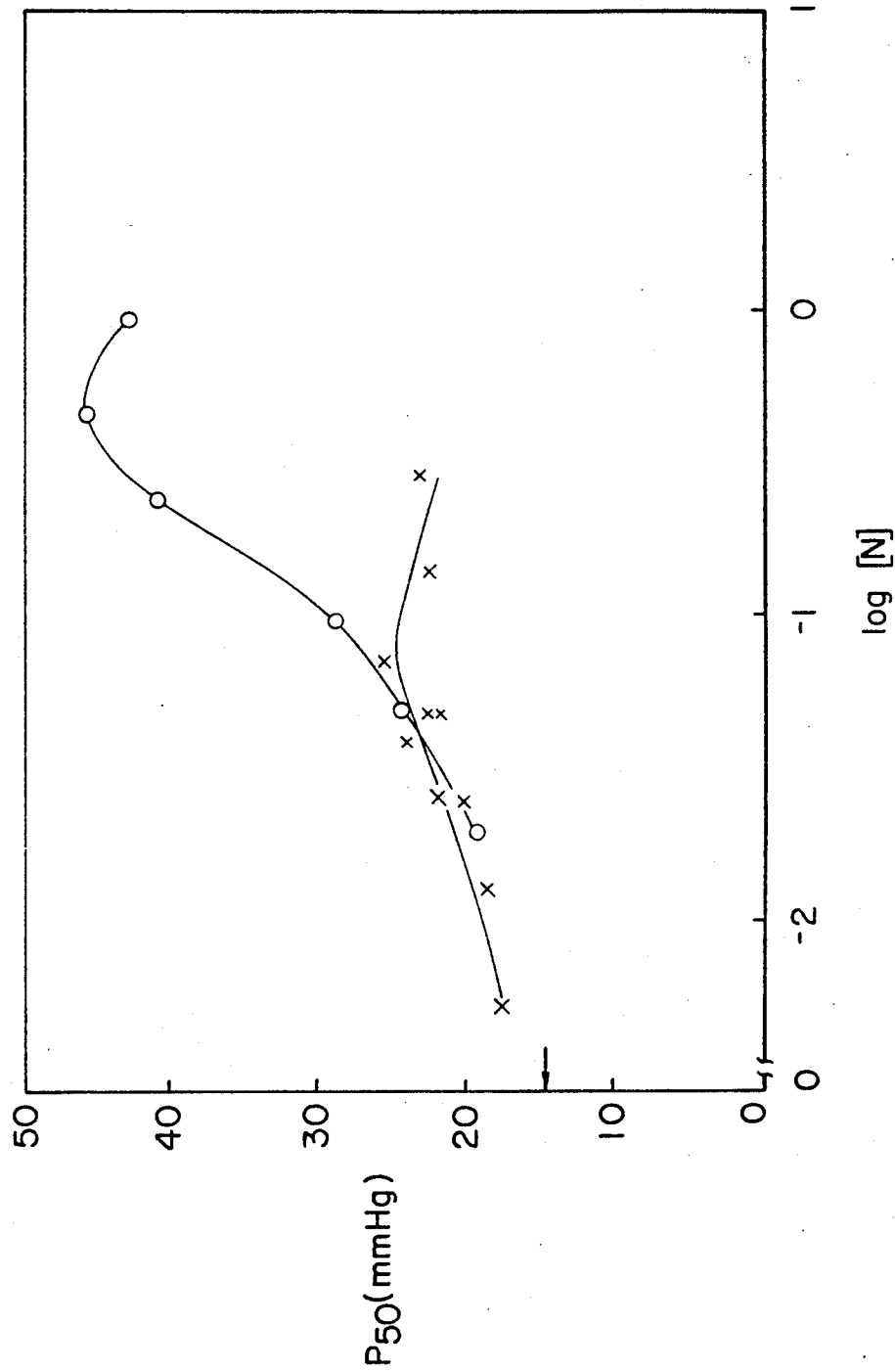
FIG. 2 shows the oxygen affinity of bovine Hb in 0.15 M Hepes buffer (pH 7.4) at 37° C., in the presence of increasing concentrations of 2,3-DPG (x) or Cl. (o). The concentration of the effectors is expressed in equivalents/liter [N], assuming that 2,3-DPG carries 5 negative charges. Protein concentration 80 mg/ml.
Figure 3:
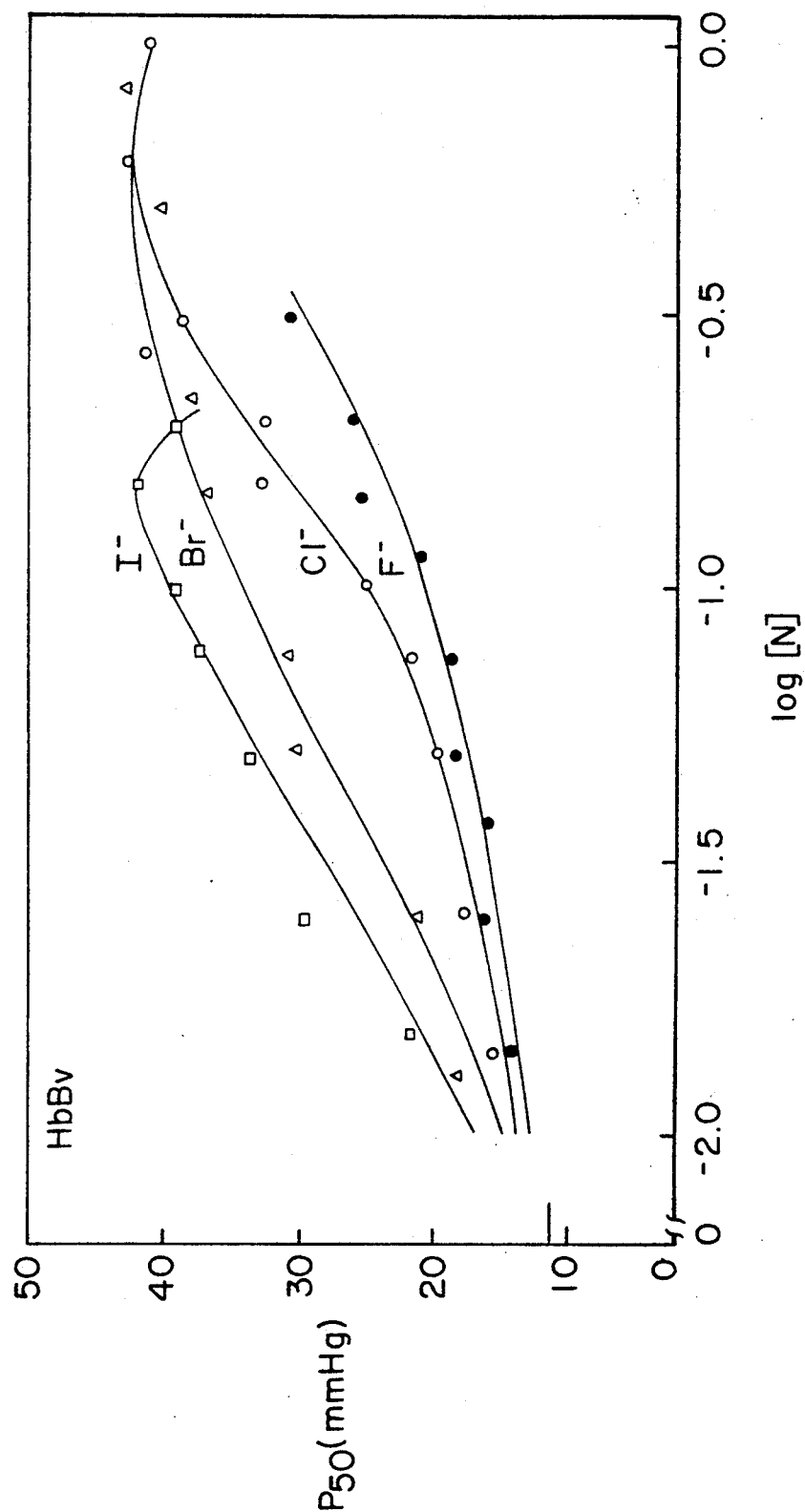
FIG. 3 shows the oxygen affinity of bovine Hb in Tris buffer at pH 7.4, in the presence of increasing concentrations of halides, expressed in equivalent/L [N].

FIG. 8 shows the chromatographic elution pattern of mutant NA1 (1) Val→Met; NA2 (2) His deleted; HCl (144) Lys→Arg. The dashed peak is collected. In electrophoresis (Beckman Paragon) a single band is produced.

FIG. 9 shows oxygen equilibrium curves of native HbA (·), Hb reconstituted from recombinant β-globin (□) and mutant Hb (Δ) NA1(1) Val→Met; NA2 (2) His deleted; HCl Lys (144)→Arg. Conditions 10 mM Pi, 100 mM NaCl, pH 7.35 at 25° C.

FIG. 10 shows the chromatographic elution pattern of the mutant β-E11 (67) Val→Thr. The peak marked Hbm is collected. In electrophoresis it produces a single band.

FIG. 11 shows the oxygen equilibrium curve of Hb βE11 (67)Val→Thr, the oxygen equilibrium curve of Hb βA1(4)Thr→Asp at pH 7.36 and of native human Hb. Conditions as in FIG. 9.

FIG. 12 shows the Bohr effect of βE11(67)Val→Thr. The oxygen equilibrium curves are measured at 25° C. Buffer 10 mM Phosphate, 80 mM NaCl, 100 mM Borax.

FIGS. 13 A and B show the amino acid and nucleotide sequence for the A1(4)Thr→Asp mutant.

FIGS. 14 A and B show the amino acid and nucleotide sequence for NA1 (1) Val→Met; NA2 (2) His deleted; HCl (I44) Lys→Arg.

DETAILED DESCRIPTION OF THE INVENTION

One object of the present invention is to incorporate aspects of bovine sequence into human β-globin such that low affinity human Hb variants with reduced immunological risk will be produced. Expressed in microorganisms, these oxygen carriers will be free of infective agents.

An urgent need exists among the medical community for an alternative to whole blood or red blood cells for use in transfusion. In response to this need, genetically engineered mutants of human Hb are being investigated for possible use as artificial oxygen carriers. However, the possibility of transmitting viral infections is ever present in derivatives of human blood. The rapid spread of the AIDS virus as well as the discovery of multiple forms of the virus amplifies this concern.

In order to explore non-human sources for a suitable oxygen carrier, bovine Hb has been studied by the inventors. Bovine Hb is particularly attractive in this regard, since it has a low oxygen affinity, a property required for artificial oxygen carriers. In fact, while the oxygen affinity of whole blood is similar in all mammalian species, the oxygen affinity of cell-free Hb solutions shows wide species variability. Bovine hemoglobin has essentially the same oxygen affinity ($P_{178}$ =27 torr at 37° C.) as whole blood under the conditions found in blood plasma (Cl 0.1 M). Solutions of human Hb at similar Cl. concentrations have a $P_{178}$ of approximately 15 torr.

The protein sequence of natural human hemoglobin is known. Moreover, the DNA sequences coding for the α and β chains of human hemoglobin are known. The present inventors, recognizing and identifying the mechanism of oxygen affinity modulation in both bovine and human hemoglobin, have identified the regions in bovine hemoglobin responsible for properties which would be desirable if present in human hemoglobin.

The present inventors have cloned and sequenced the β-chains of a modified or mutant human hemoglobin that has at least one additional chloride binding site than natural human hemoglobin. Although natural human hemoglobin may contain chloride binding sites, these sites in human hemoglobin do not efficiently regulate the affinity for oxygen in vivo. By incorporating at least one additional chloride binding site into human hemoglobin, the inventors have been able to lower the oxygen affinity constant of the modified hemoglobin relative to natural hemoglobin.

Human hemoglobin has an oxygen affinity ($P_{50}$ in mmHg) of 15 mmHg, pH 7.4 at 37° C., 0.1 M Cl. Bovine hemoglobin under the same conditions has an oxygen affinity of ($P_{50}$) of 28 mmHg. Moreover, under the same conditions, human hemoglobin has a chloride affinity of $100M^{-1}$, whereas bovine hemoglobin has a chloride affinity of 500 $M^{-1}$. (C. Fronticelli et al, J. Biol. Chem., 259, 10841–10844 (1984)).

With respect to natural human Hb, the presence of chloride has a small effect on the oxygen affinity constant. The present inventors have found that by adding at least one additional chloride binding site into natural human Hb, the oxygen affinity constant is decreased and as a consequence, the affinity for oxygen is reduced.

Thus, although there are chloride binding sites present in natural human Hb, it was the present inventors who for the first time have engineered a modified human Hb molecule where the oxygen affinity is efficiently modulated by chloride. The chloride site is added to human Hb by selected amino acid mutations to create a chloride binding site. The chloride binding site is not represented by any unique sequence of amino acids. Rather, by introducing positive charges in specific positions of the hemoglobin by the incorporation of positively charged amino acids, the resulting conformation of hemoglobin is capable of being regulated by chloride.

The new chloride binding site is oxygen-linked in the sense thta it is most active in the modified human Hb when the Hb is not bound with oxygen. When the oxygen is released, the Hb changes conformation and the Hb binds $Cl^-$. Thus, the binding of $Cl^-$ ions to hemoglobin elicits the release of more molecules of $O_2$ from hemoglobin. In this way the affinity of Hb for $O_2$ is regulated by chloride. The chloride binding site requires one, two or more positive charges along with a suitable conformation so the chloride binds preferentially to the oxygenated Hb. The presence of oxygen causes a change in conformation of the Hb molecule thereby releasing the chloride.

As discussed above, chloride binding sites are made by introducing positive charges in the Hb. These positive charges are introduced by substituting uncharged or negatively charged amino acids with positively charged amino acids into the Hb, preferably into the β-chain. Preferable positively charged amino acids include arginine, lysine and histidine. Substituting in the molecule hydrophobic amino acids for hydrophilic amino acids or vice versa could produce a change in the conformation of the Hb which contributes to the formation of additional chloride binding sites.

Therefore, the modified human Hb of the invention will have low oxygen affinity. Stabilization of the tetramer will be attained by introducing Cys-S-S-Cys crosslinks between the α-chains, the β-chains or both. Alternatively, the tetramer may be stabilized by chemical crosslinks or pseudocrosslinks between the α-chains, β-chains or both. (See U.S. Ser. No. 321,682 filed Mar. 10, 1989). For instance, a dimer containing an α-β chain may cross-link with another α-β dimer in such a manner that the α chains covalently bond together to form a stable tetramer or the β-chains covalently bond together to form a stable tetramer.

Possible commercial and medical applications of the modified hemoglobin include uses as synthetic blood which may be injected into a patient with a physiologically acceptable injectable carrier such as physiological saline and Ringer solution.

The present inventors also disclose DNA (e.g., cDNA) clones coding for modified human hemoglobin including the unmodified α-chains and the modified β-chains. The methodology for construction and isolation of the DNA clones of the present invention is described in detail below.

Another aspect of the present invention provides a method for producing the novel polypeptide of the β-chain of modified human hemoglobin.

The method of the present invention involves culturing a suitable microorganism or cell, which has been transformed with plasmids which code for the novel β-chains of the invention.

Suitable vectors for use in the method of expression of the modified human hemoglobin of the invention may contain the full novel DNA sequences coding for the β-chains of hemoglobin, a segment thereof, or the entire DNA sequence coding for hemoglobin including both the α and β-chain. The vectors may also contain appropriate expression regulatory sequences. Any suitable vector capable of expressing a protein may be used.

| Amino Acid | Three-letter abbreviation | One-letter symbol |
| --- | --- | --- |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamine acid | Glu | E |
| Glutamine or glutamic acid | Glx | Z |
| Glycine | Gly | G |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Recombinant β-chains of hemoglobin can be recovered from cultures by lysing the cells to release the β-chains present inside the cells in the form of fusion protein or as a β-chain per se. Initially, cell debris can be separated by centrifugation. The remaining debris and the supernatant are then repeatedly treated with solvents in which the cell debris are soluble but in which the β-chain hemoglobin is not soluble to thereby precipitate β-chain hemoglobin. These procedures can be repeated and combined with other procedures including filtration, dialysis and/or chromatography to obtain a pure product. Enzymatic cleavage of the fusion protein may be necessary.

In accordance with degeneracy of genetic code, it is possible to substitute at least one base of the base sequence of a gene by another kind of base without causing the amino acid sequence of the polypeptide produced from the gene to be changed. Hence, the DNA of the present invention may also have any base sequence that has been changed by substitution in accordance with degeneracy of genetic code.

The DNA is readily modified by substitution, deletion or insertion of nucleotides, thereby resulting in novel DNA sequences encoding β-chain hemoglobin or its derivatives. These modified sequences are used to produce mutant β-chain hemoglobin and to directly express β-chain hemoglobin.

DNA regions are operably linked when they are functionally related to each other. For example, DNA for a presequence or secretory leader is operably linked to DNA for a polypeptide if it is expressed as a preprotein which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading phase.

Suitable host cells are prokaryotes, yeast or higher eukaryotic cells. Prokaryotes include gram negative or gram positive bacteria, for example E. coli or Bacilli. Higher eukaryotic cells include established cell lines of insect, spider or mammalian origin as described below.

Prokaryotic host-vector systems are preferred for the expression of β-chain hemoglobin. A plethora of suitable microbial vectors are available. Generally, a microbial vector will contain an origin of replication recognized by the intended host, a promoter which will function in the host and a phenotypic selection gene, for example, a gene encoding proteins conferring antibiotic resistance or supplying an auxotrophic requirement.

Vectors must contain a promoter which is recognized by the host organism. This is generally a promoter homologous to the intended host. Promoters most commonly used in recombinant DNA construction include the β-lactamase (penicillinase) and lactose promoter systems, a tryptophan (trp) promoter system and the tac promoter. While these are the most commonly used, other known microbial promoters are suitable. Details concerning their nucleotide sequences have been published, enabling a skilled worker operably to ligate them to DNA encoding β-chain hemoglobin in plasmid vectors and the DNA encoding β-chain hemoglobin. At the present time a preferred vector is pKJ05.

In addition to prokaryates, eukaryotic microbes such as yeast cultures may be transformed with β-chain hemoglobin encoding vectors. Saccharomyces cerevisiae, or common baker's yeast, is the most commonly used among lower eukaryotic host microorganisms, although a number of other strains are commonly available. Yeast vectors generally will contain an origin of replication from the 2 micron yeast plasmid or an autonomously replicating sequence (ARS), a promoter, a DNA sequence coding for β-chain hemoglobin, sequences for polyadenylation and transcription termination and a selection gene.

Suitable promoting sequences in yeast vectors include the promoters for metallothionein, 3-phosphoglycerate kinase or other glycolytic enzymes.

Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. In constructing suitable expression plasmids, the termination sequences associated with these genes are also ligated into the expression vector 3' of the β-chain hemoglobin coding sequences to provide polyadenylation of the mRNA and termination.

In addition to microorganisms, cultures of cells derived from multicellular organisms may also be used as hosts. In principal, any higher eukaryotic cell culture is workable, whether from vertebrate or invertebrate culture. However, interest has been greatest in vertebrate cells, and propagation of vertebrate cells in culture (tissue culture) has become a routine procedure in recent years. Examples of useful host cell liens are VERO and HeLa cells, Chinese Hamster overy (CHO) cell lines, and WI38, BHK, COS-7 and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and most preferably Simian Virus 40 (SV40). The early and late promoters are particularly useful because both are obtained easily from the virus as a fragment which also contains the SV40 viral origin of replication. Smaller or larger SV40 fragments may also be used, provided the approximately 250 bp sequence extending from the Hind III site toward the BglI site located in the viral origin of replication is included.

An origin of replication may be provided either by construction of the vector to include an exogenous origin, such as may be derived from SV40 or other viral (e.g., Polyoma, Adenovirus, VSV, or BPV) source, or may be provided by the host cell chromosomal replication mechanism. If the vector is integrated into the host cell chromosome, the latter is often sufficient.

The vector actually utilized for expression of mutant β-globin fusion proteins is a derivative of pAS1 (M. Rosenberg, et al. (1982) Met. Enzymol. 101, 123), where the NS1 gene from influenza A virus is cloned into the Bam HI site (J. F. Young, et al. (1983) Proc. Natl. Acad. Sci USA 80, 6105). A linker coding for the recognition sequence of blood clotting Factor $X_a$ is inserted into the NcoI site of the NS1 gene. The human β-globin cDNA (obtained by Dr. B. Forget, Yale University) is inserted 3' to the factor X recognition sequence giving a plasmid similar to that described previously by Nagai and Thogersen (1984), Nature 308, 810. High expression levels of the NS1-FX-β-globin fusion protein are obtained using E. coli AR58 transformed with this plasmid (pJK05). Mutant β-globin genes are obtained using appropriate oligonucleotides and linearized pJK05 by conventional polymerase chain reaction technique (PCR Technology: Principles & Applications for DNA Amplification, H. A. Erlich, Editor, Stockton Press, 1989). After hydrolysis of the PCR product with NcoI and EcoRV, it is ligated into pJK05 which has been treated with the same two restriction enzymes, thereby replacing the native β-globin gene with the mutant gene.

A. Site-Specific Mutagenesis

The generation of site-specific mutants has become a relatively straightforward procedure due to two developments, the Polymerase Chain Reaction (PCR) and the Kunkel methods. The present inventors employ both techniques.

A schematic of the NS1-FX-β-globin portion of pJK05 is shown below.

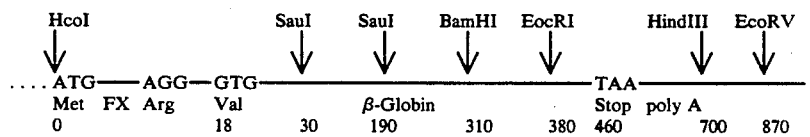

The regions where mutations are desirable are: a) between the NcoI and the first SauI site; b) between the second SauI site and the BamHI site; and c) between the EcoRI site and the stop codon. Convenient restriction sites exist for making the mutants in regions a and c by the PCR method (PCR Technology: Principles & Applications for DNA Amplification, H. A. Erlich, Editor, Stockton Press, 1989). The mutations in region b will be made by the Kunkel method (Proc. Natl. Acad. Sci. USA, 82, 488 (1985) and Meth. Enzymol., 154, 376 (1987)). The latter method is used for making several β-globin mutants, following the excellent protocol provided by Bio-Rad Laboratories for their "Muta-Gene M-13 In Vitro Mutagenesis Kit". The PCR method will be used for making mutations at the 5, and 3' ends of the β-globin gene because this technique will allow other changes in the DNA sequence which will facilitate subsequent manipulation of the DNA.

For the 5'-end mutants, oligonucleotides will be synthesized which alter the protein sequence from Val-His-Leu-Thr to Met-Leu-Thr, in accordance with mutation 1 above, and also eliminate the first SauI site replacing it with another unique restriction site in the same vicinity. This will leave the second SauI site a unique site in the plasmid and enable regions bearing each of the mutations to be moved from plasmid to plasmid. A similar approach can be used to make the HCl Lys-Arg mutation near the 3'-end of the gene, and at the same time remove the poly A tail region which is a factor in the plasmid instability encountered in plasmids bearing both $\alpha$ and $\beta$-globin genes. The sequences of the oligonucleotides will also be altered in accordance with preferred codon usage in *E. coli* (Grosjean et al, Gene, 18, 199-209 (1982)). The Arg codons of globin cDNA's appear to be particularly unfavorable for *E. coli* expression.

The invention is also directed to a novel method of reconstituting native hemoglobin which does not require the extensive purification of the $\beta$-chains as described by other methods (Nagai et al, Proc. Natl. Acad. Sci. USA, 82, 7552 (1985)). According to this method, the partially purified $\beta$-chain fusion protein is dissolved in alkali and partially renatured by extensive dialysis at pH 8 to 9 in the presence of an S—S bond reducing agent. After enzymatic cleavage with $FX_a$ the $\beta$-globin separates from the remaining fusion protein. Addition of heme and native $\alpha$-subunits reconstitute a native Hb, modified at the $\beta$-chains. The modified Hb is purified from all unwanted material by ion exchange chromatography or other suitable procedure (e.g., affinity chromatography).

Specific goals of this invention are:

1) to introduce by site directed mutagenesis specific amino acid substitutions in the cloned $\beta$-chains of human Hb in order to produce Hb variants where the oxygen affinity is efficiently modulated by the interaction with the chloride ions;
2) to introduce by site directed mutagenesis amino acids which may mimic the effect of 2,3-DPG, preferably by introducing negatively charged amino acids (e.g., Asp or Glu) at the N-terminal residues of the $\beta$-chains;
3) to introduce by site directed mutagenesis amino acids which may stabilize the deoxy form of Hb, preferably by introducing hydrophobic amino acids (e.g., Ala, Gly, Leu, Met, Phe, Pro, Ser, Thr, Trp, Tyr or Val) at the N-terminal residues of the $\beta$-chain; and
4) to purify the mutant $\beta$-chains, reconstitute them with heme and combine with $\alpha$-chains giving the mutant hemoglobin molecule.

The following are characteristics of HbBv which will be introduced individually and collectively in the modified human hemoglobin.

B. Functional Characteristics of Bovine Hemoglobin a. Interaction with Chloride Ions

The low oxygen affinity of HbBv results from an increased preferential binding by deoxy hemoglobin of monovalent anions present in the solution. FIG. 1 shows the effect of increasing chloride concentrations of the $P_{50}$ of human (○) and bovine (●) hemoglobin. Measurements are done at 37° C., at pH 7.4, in a Tris buffer. The protein concentration is 80 mg/ml. In the abscissa the molarity of the buffer is equal to the anion concentration. The data indicate a different response of the oxygen affinity in the two hemoglobins with increasing $Cl^-$ concentration. Extrapolation of the two curves to zero chloride concentration shows that in the absence of anions, the oxygen affinity of human and bovine Hbs are similar. This indicates that the different affinity for oxygen of the two proteins is due to a higher preferential binding of $Cl^-$ ions to the deoxy-form of bovine Hb. As reported by Fronticelli et al (J. Biol. Chem., 259, 10841-10844 (1984)), from the slopes of the curves in FIG. 1 it is possible to calculate that deoxy bovine Hb upon oxygenation liberates one more chloride ion per tetramer than human Hb.

The positive slope of the curve in FIG. 1 indicates that $Cl^-$ ions are released upon oxygenation. The negative slope is due to absorption of $Cl^-$ by the Hb dimers formed at high ionic strength. From the positive slope of the curves it was calculated that bovine deoxy-Hb binds two $Cl^-$ ions/tetramer more than its oxy derivative, whereas deoxy human Hb binds only one more. The higher sensitivity to $Cl^{-1}$ ions of bovine Hb provides a rationale for the modulation of oxygen affinity by $Cl^-$ in the physiological concentration range near 0.1 M. Such control thus provides an excellent alternative to the more common mechanism of regulation of oxygen affinity by organic phosphates as seen in other vertebrates.

b. Interaction with 2,3-DPG

In FIG. 2 the effect of 2,3-DPG and $Cl^-$ on the oxygen affinity of bovine Hb ar compared. The anion concentration is expressed in equivalents/L(—[N]) and the assumption is made that the five ionizable groups of 2,3-DPG are fully charged. The results indicate that in bovine Hb there are high affinity sites for anions (detectable at $Log[N] < -1.2$) equally accessible 2,3-DPG and $Cl^-$, and low affinity sites (detectable at $log[N] > -1.2$) not accessible to 2,3-DPG. As a consequence, at the physiological concentration of $Cl^- Log[N] = -1$), bovine Hb has a lower oxygen affinity than it does in the presence of equimolar or higher concentrations of 2,3-DPG.

c. Interaction with Halide Ions

In view of the effect of $Cl^-$ on the oxygen affinity of bovine Hb, the present inventors have explored the effect of other monovalent anions. FIG. 3 shows the oxygen affinity of bovine Hb in the presence of increasing concentrations of halides. In bovine Hb the maximum value of $P_{50}$ is similar for $I^-$, $Br^-$ and $Cl^-$, however, the anion concentration range within which the maximum occurred is in the order $I < Br < Cl < F$. The above data suggest that the bovine Hb molecule could discriminate among halides on the basis of their charge density. The property to distinguish between monovalent anions is peculiar to the bovine Hb system and is not present in human Hb. Competition experiments using mixtures of the various anions show that the halides bind to the same sites in the bovine Hb molecule (Fronticelli, C. et al, J. Mol. Biol., 202, 343-348 (1988)).

C. Formulation of a model for the regulation of oxygen affinity by Cl⁻ ions a. Hydropathic Characteristics of the Hemoglobin Molecule

Figure 4:
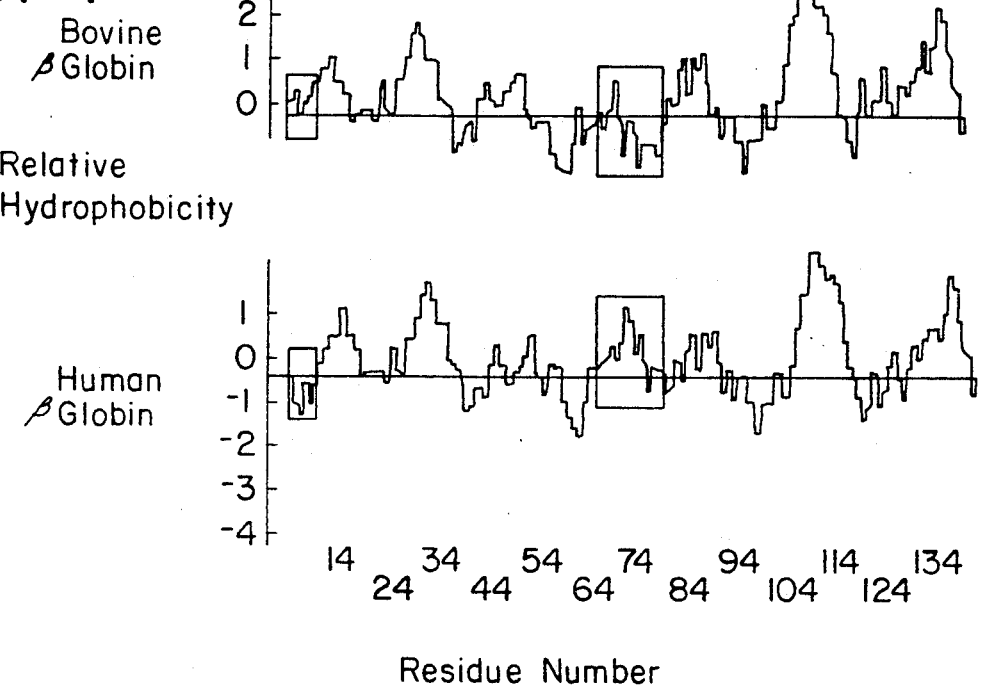
FIG. 4 shows hydropathy plots of bovine and human β-chains; the squares indicate the two regions of opposite hydrophobicity. These plots are obtained using the hydrophobicity values derived by Kite et al (J. Mol. Biol., 157, 105–132 (1982)).
Figure 5:
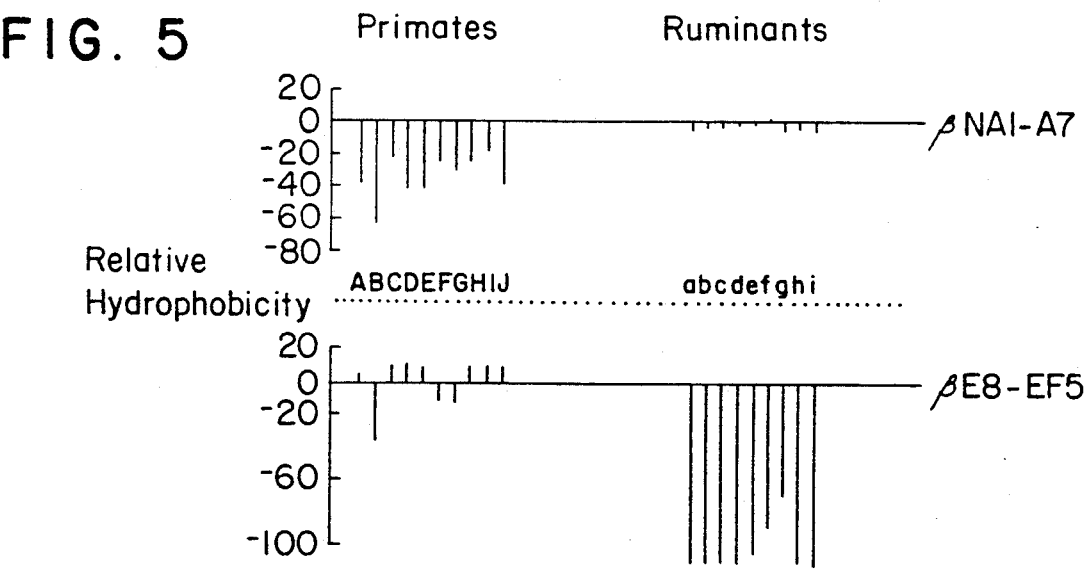
FIG. 5 shows a histogram of the hydrophobicity values calculated for the regions βNA1–A7 (top) and βE8-EF5 (bottom) of the β-chains of the primate and ruminant hemoglobins listed in Table III.

The hydropathic characteristics of the α and β chains of human and bovine Hbs obtained using the hydrophobicity values derived by Kite et al (J. Mol. Biol., 157, 105-132 (1982)) are shown in FIG. 4.

Two regions of opposite hydrophobicity are evident, one comprising residues at the amino terminal end, the other residues at the E-helix and EF-corner. The hydropathy plots of the α and β chains of the primate and ruminant Hbs listed in Table III are very similar to the profiles obtained for human and bovine Hbs respectively (see FIG. 4).

TABLE III

List of primate and ruminant hemoglobins analyzed for their hydropathic characteristics
β-Globins analyzed

| Primates | | Ruminants | |
|---|---|---|---|
| (A) | Human, chimpanzee, and gorilla | (a) | Bovine |
| (B) | Rhesus mOacaque, Japanese | (b) | Gayal |
| | | (c) | Yak |
| | | (d) | Greater kudu |
| (C) | Spider monkey | (e) | European moose |
| (D) | Black and red tamarin | (f) | Virginia white-tailed deer |
| (E) | Brown headed tamarin | (g) | Sheep |
| (F) | White fronted capuchin | (h) | Goat β-A chain |
| (G) | Brown capped capuchin | (i) | Goat, sheep β-C chain |
| (H) | Common gibbon | | |
| (I) | Night monkey | | |
| (J) | Common squirrel monkey | | |

Figure 8:
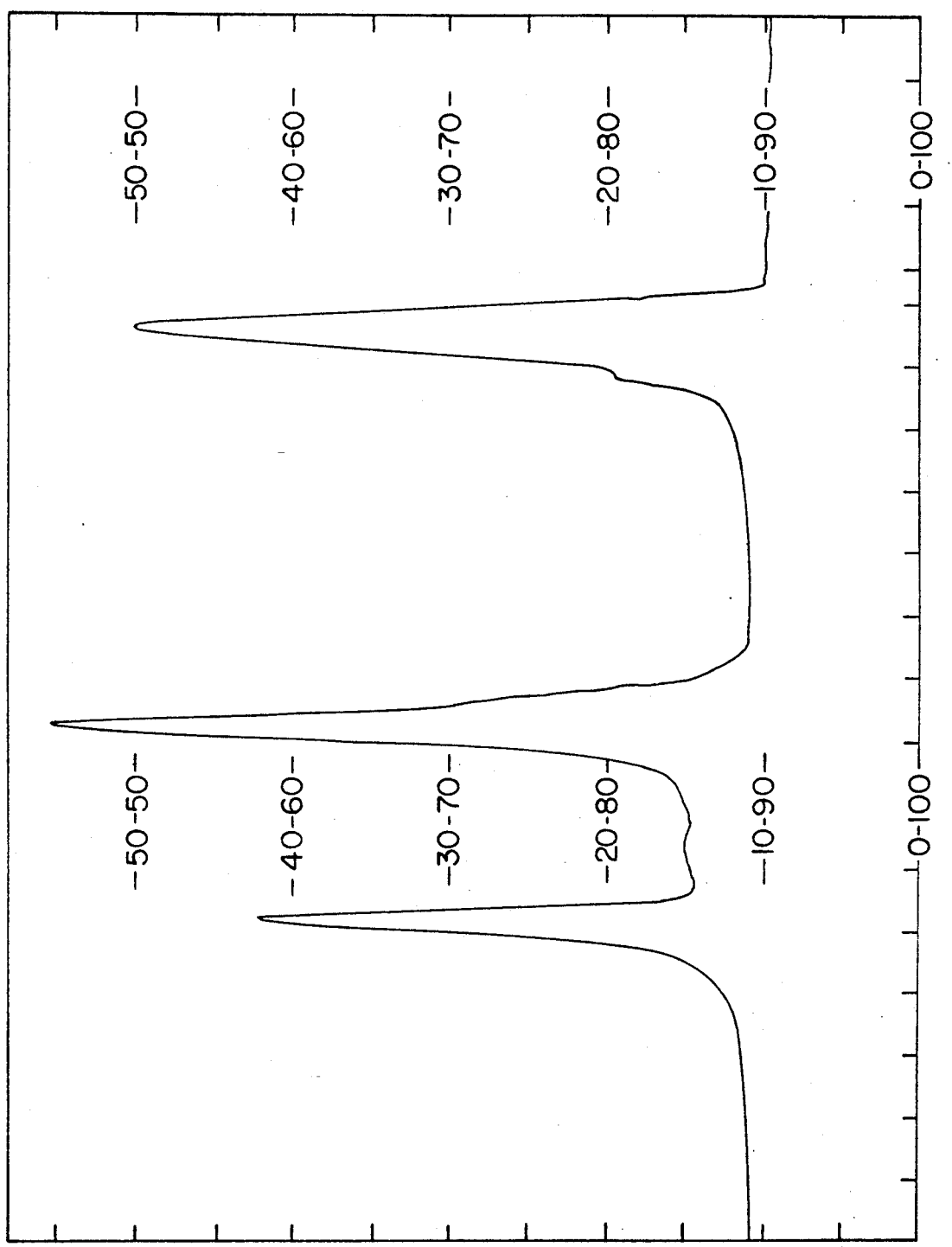

The histogram of the average hydropathy values obtained from the two regions of opposite hydrophobicity in primate and ruminant β-chains is shown in FIG. 8. The bars correspond to the average of the values of each region, respectively, for the segment NA-1-A7β and E8-EF5β, of the various primate and ruminant β-chains.

In order to determine whether these differences are consistent with the use of other hydrophobicity scales, a similar analysis was performed using either the consensus scale of Eisenberg et al (Faraday Symp. Chem. Soc., 17, 109-120 1982)), which represents the mean of four different hydrophobicity scales, or the OMH (optimal matching hydrophobicity (Eisenberg et al, Faraday Symp. Chem. Soc., 17, 109-120 (1982)) scale which was derived directly from the hydrophobicities of amino acids in the globin family. Table IV shows the global average values calculated for the various sets. Although, as expected, the absolute values differ, in all cases the analysis confirms the presence of different regions of hydrophobicity between primate and ruminant β-chains.

TABLE IV

Hydrophobicity values of the regions NA1-A7 and E8-EF5 of primate and ruminant β-chains
The values are the average of 10 sequences for primates and 9 sequences for ruminants.

| Hydrophobicity scale | Primates (Sequence) | Ruminants (Sequence) |
|---|---|---|
| | (βNA1-A7[1–10]) | (βNA1-A7[1–9]) |
| Kite and Doolittle | −3.34 | −0.08 |
| Composite | −3.93 | 3.18 |
| OMH | −20.0 | −13.0 |
| | (βE8-F5[64–81]) | (βE8-EF5[63–80]) |

TABLE IV-continued

Hydrophobicity values of the regions NA1-A7 and E8-EF5 of primate and ruminant β-chains
The values are the average of 10 sequences for primates and 9 sequences for ruminants.

| Hydrophobicity scale | Primates (Sequence) | Ruminants (Sequence) |
|---|---|---|
| Kite and Doolittle | 0.150 | −92.8 |
| Composite | 13.6 | −25.0 |
| OMH | 13.34 | −47.0 |

Negative values indicate the degree of hydrophilicity of the polypeptides; positive values indicate their degree of hydrophobicity. These data clearly show that the amino terminal residues NA1-A7β of the β-chains of ruminants are more hydrophobic than in primates, this effect being reversed in the E8-EF5β region.

Since 28% of the amino acid residues of bovine Hb are different from human Hb, bovine Hb would be expected to be more immunogenic than human Hb for human subjects. However, a careful comparison of bovine and human HBs provides insight into amino acid replacements which would lower the oxygen affinity of human Hb.

In order to correlate the different hydrophobicity of residues βNA1-A7 and βE8-EF5 with differences in amino acid composition, the present inventors have compared the sequences of these residues in primate and ruminate β-chains. The results in Table V show the presence of constant substitutions between primate and ruminant Hbs.

TABLE V

Constant amino acid substitutions in the regions βNA1-A7 and βE8-EF5 in primate and ruminant β-chains
β-globin

| Primates (10 sequences) | Ruminants (9 sequences) |
|---|---|
| NA1(1) Valine | Methionine |
| NA2(2) Histidine | deleted |
| A2(5) Proline | Alanine |
| E13(69) Glycine | Aspartic acid |
| E14(70) Alanine | Serine |
| E18(75) Leucine | Methionine |
| E20(76) Alanine | Lysine |
| HCl(144) Lysine | Arginine |

Another constant difference is the presence in ruminant β-chains of an arginine at position βHCl replacing a lysine at that position in human Hb. Arginine is expected to be a better ligand for Cl⁻ than lysine because a guanidinium ion can form two hydrogan bonds to Cl⁻, whereas an alkylammonium ion can form only one.

An aspect of this invention is based on the idea that during the evolutionary process, these substitutions have been selected for introducing into ruminant Hbs an increased sensitivity to Cl⁻, responsible for the lowered oxygen affinity of these Hbs.

On the basis of these observations a model is proposed for explaining the regulation of oxygen affinity by chlorides, as an alternative to the classic modulation by 2,3-DPG.

b. Proposed Model

In this model, the binding of Cl⁻ ions is modulated by a displacement of the A-helix of the β-chain, governed by the characteristics of the N-terminal residues. This type of control of oxygen affinity constitutes an alternative to the regulation by organic phosphate within the red cells and would be very efficient in the regulation of oxygen affinity in a solution of hemoglobin at physiological concentration of Cl− ions.

Figure 9:
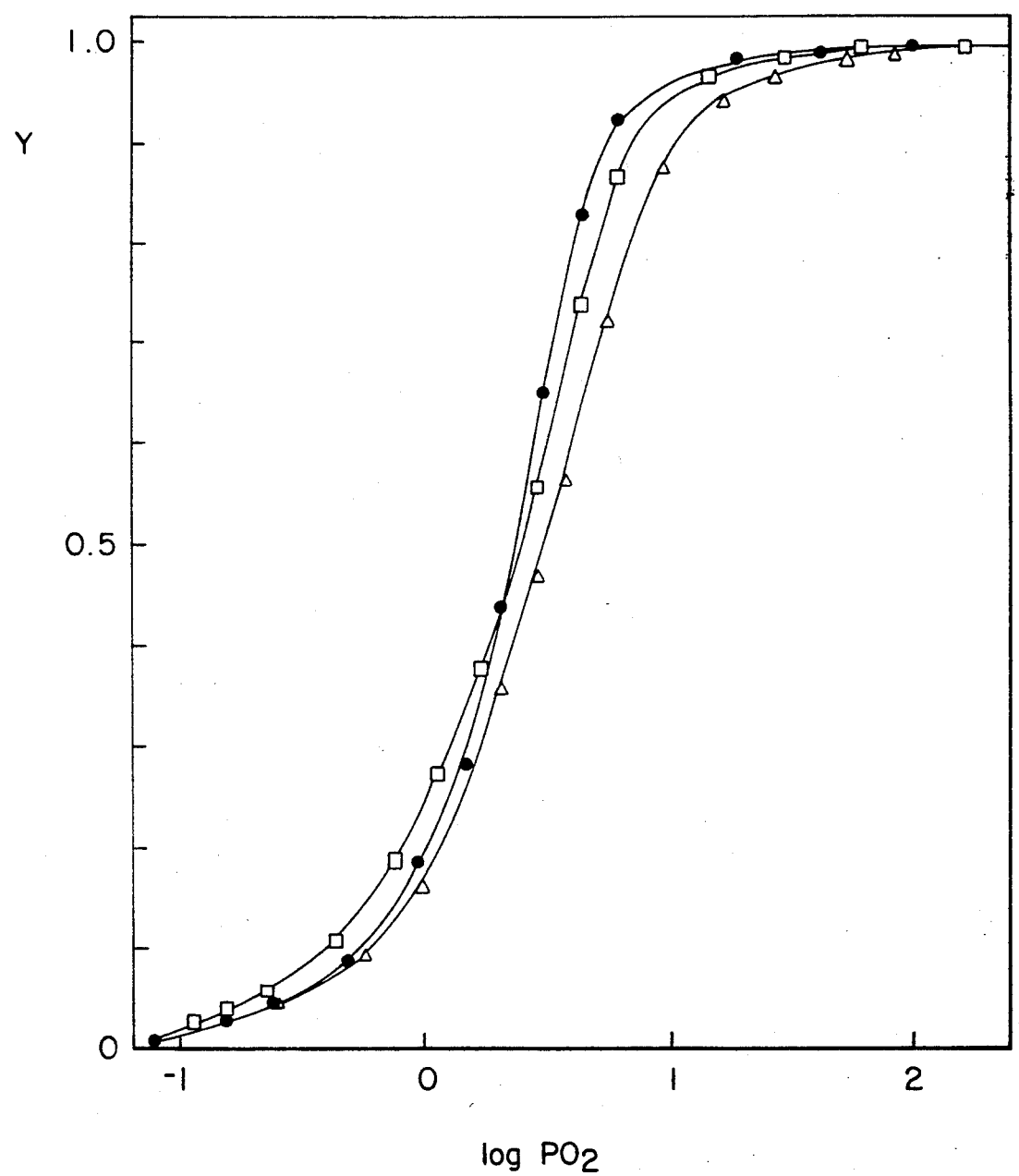

The following two mechanisms are proposed which associate the movement of the amino-terminal residues of the β-chains to the formation of the extra oxygen-linked chloride-binding sites present in ruminant Hbs. They do not exclude each other. The rationale for this hypothesis is illustrated in FIG. 9 which shows the two β-chains of human Hb viewed along the two-fold symmetry axis. The full circles represent the position of the consistent amino acid substitutions mentioned in Table IV, and the positive signs identify the residues involved in the formation of the Cl− binding sites. The chloride ions are themselves represented by the open circles containing a negative sign. The arrows at the N-terminal end suggest the movement of this portion of the A-helix in the transition between the oxy and deoxy conformation.

i) An Anion Binding Site Formed by Lys-A5β, Lys-E20β and His-E21β

The rationale for this binding site is as follows: in the transition to the deoxy form, the hydrophobic side chain of the N-terminal methionine moves toward the interior of the protein producing a distortion of the A-helix. This in turn, results in the displacement of Lys-A5β toward the E-helix. In ruminant Hbs, a positively charged lysine replaces an alanine at position E20β of human Hb. This substitution together with the distortion of the A-helix results in the formation of a cluster of three positively charged amino acid side chains, Lys-A5β, Lys-E20β, His-E21β, which define a Cl− binding site. Binding of the Cl− ions would be modulated by movement of the Lys-A5β brought about by the different positioning of the N-terminal end of the A-helix in the oxy and deoxy forms. In bovine hemoglobin the presence of hydrophilic residues at position E13β, E14β and E19β may help the formation of the cluster by contributing a slight distortion of the E-helix which helps to correctly juxtapose the three residues of the cluster. In this way an oxygen linked Cl− binding site is formed which is most active in the oxygenated Hb.

ii). An Anion Binding Site at Arg-HClβ

The rational for this binding site is as follows: as discussed above, arginine is a better ligand to Cl− than lysine because a guanidinium ion can form two hydrogen bonds to the anion whereas an alkyl ammonium ion can form only one. Arg-HCl is positioned in the β-cleft, the same region where 2,3-DPG binds to human Hb. In the deoxy conformation this arginine may function as a ligand in the binding of Cl− ions. In the oxy form the movement of segment NA1-A7 toward the central cavity would position the hydrophobic NA1 methionine in the proximity of the arginine HCl of the partner β-chain. As a result, the affinity of arginine HCl for Cl− ions decreases and the Cl− ions are released upon oxygenation. In this way an oxygen linked Cl− binding site is formed which is most active in the oxygenated Hb.

Human Subjects

Human hemoglobin is prepared from blood samples obtained from the Blood Bank of the University of Maryland Hospital. The samples do not carry identifier and would be otherwise discarded.

The following non-limiting Examples describe how to make the modified human hemoglobin of the invention including how to purify the cloned β-globin and how to reconstitute the α and β chains to form functional hemoglobin.

EXAMPLES

Example 1

Expression of Globins in *E. coli*

The construction of plasmids of the Nagai and Thogersen type to produce a more soluble β-globin fusion protein, thereby facilitating the renaturation procedure is described in O'Donnell et al, Biochemistry, 24, 3375 (1985) and Brinigar et al, Symp. of Oxygen Binding Heme Proteins, Oct. 9-13 (1988). The most successful plasmid utilized in the present invention is diagrammed in FIG. 10.

Figure 10:
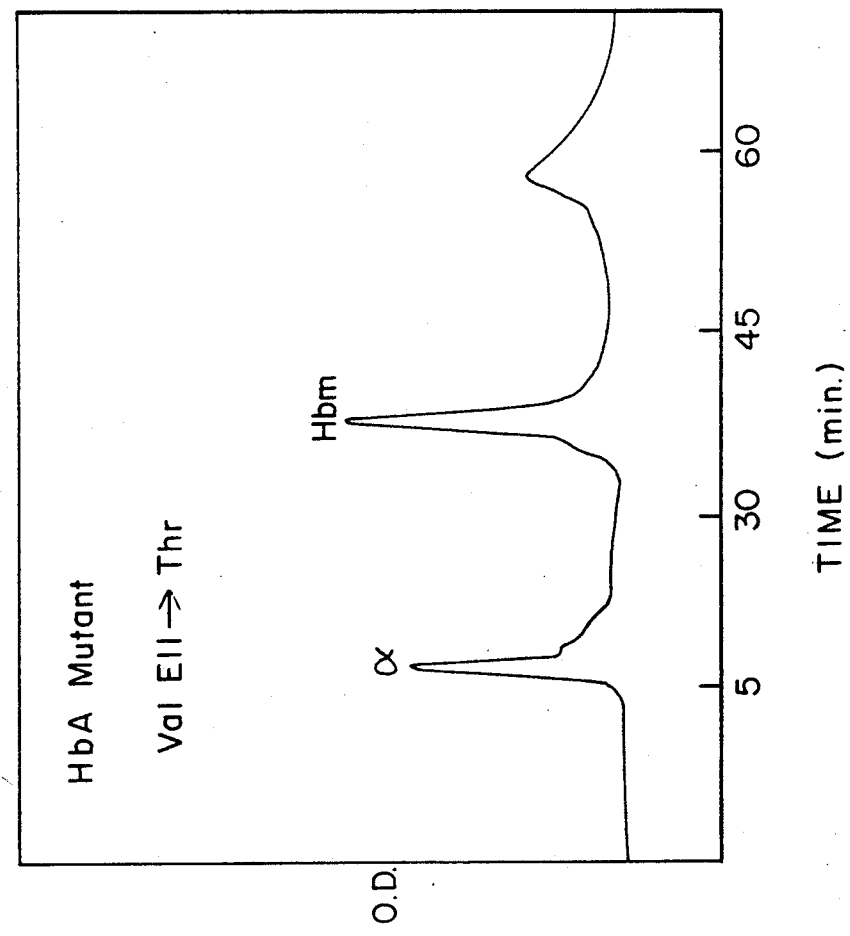

Although several types of plasmids (e.g., Nagai-Thogersen type) may be used where all the fusion protein expressed are found in the cell lysis pellet, the NS1-FX-βglobin (pJK05) protein is found to be more readily solubilized, cleaved with Factor Xa and renatured, than the Nagai-Thogersen fusion protein. For that reason, pJK05 as shown in FIG. 10, will be used in this study to produce the desired β-globin mutants.

pJK05, by temperature induction produces 35 mg of fusion protein per liter of culture, and is used for these studies.

The vector actually utilized for expression of mutant β-globin fusion proteins is a derivative of pASI (M. Rosenberg, et al. (1982) Met. Enzymol. 101, 123), where the NS1 gene from influenza A virus is cloned into the Bam HI site (J. F. Young, et al. (1983) Proc. Natl. Acad. Sci USA 80, 6105). A linker coding for the recognition sequence of blood clotting Factor $X_a$ is inserted into the NcoI site of the NS1 gene. The human β-globin cDNA (obtained by Dr. B. Forget, Yale University) is inserted 3' to the factor X recognition sequence giving a plasmid similar to that described previously by Nagai and Thogersen (1984), Nature 309, 810. High expression levels of the NS1-FX-β-globin fusion protein are obtained using *E. coli* AR58 transformed with this plasmid (pJK05). Mutant β-globin genes are obtained using appropriate oligonucleotides, which are selected depending upon the particular mutant desired, and linearized pJK05 by conventional polymerase chain reaction technique (PCR Technology: Principles & Applications for DNA Amplification, H. A. Erlich, Editor, Stockton Press, 1989). After hydrolysis of the PCR product with NcoI and EcoRV, it is ligated into pJK05 which has been treated with the same two restriction enzymes, thereby replacing the native β-globin gene with the mutant gene.

Example 2

Purification of the Cloned β-Globin

*E. coli* containing the plasmid pJK05 is grown in LB+ampicillin (35 mg/l) and induced by jumping the temperature rapidly from 32° C. to 42° C. Two hours after induction the cells are harvested, lysed and centrifuged discarding the supernate. After lysis of the cells and solubilization of the *E. coli* membrane bound proteins the fusion protein is collected as an insoluble pellet. (Nagai Thogersen, *Methods in Enzymes*, Vol. 153, 19411-481). SDS -Page reveals the presence of a main component, with a M.W. of 24 Kdalton, representing about 70% of the total proteins. A Western blot, using rabbit anti-human-β-chains antisera shows a positive reaction only with this fraction, as expected for a protein containing human β-globin. These data indicate that the pellet contain the fusion protein as a pure fraction. The pellet is solubilized in oxygen free cold 0.1 M NaOH containing 1 mM Dithiothreitol (DTT) and 1 mM Ethylenediaminotetracetic acid (EDTA) and the fusion protein is diluted 10 to 50 fold with an oxygen-free solution of 40 mM borate buffer at pH 8.0, containing 1 mM DTT and 1 mM EDTA in order to reduce all the disulfide bridges. The protein is dialyzed for 3 hr against an oxygen free 40 mM borate buffer containing 1 mM DTT and 1mM EDTA followed by 2 hr dialysis against an oxygen-free solution of 40 mM borate buffer containing 0.1 mM DTT. The protein is digested for 24 hours with 1:400 (w/w) Factor Xa. Factor X is prepared in this laboratory according to the procedure of Fujikawa et al (Biochemistry, 11, 4882–4890 (1972)). Factor X is activated to FXa by viper venom as described by Nagai & Thogersen Methods in Enzymology, Vol. 153. At this time the fusion protein is almost completely cleaved and the authentic β-globin released. In SDS-Page, the product of the digestion produces a new band with a M.W. of 16 Kdalton which reacts with the rabbit anti-human-β-chains anti-sera, and has a mobility identical to β-chains prepared from natural human Hb.

Example 3

Reconstitution on the Native Hemoglobin

To the digested fusion protein of Example 2 an equimolar amount of CN-heme and native α-chains are added and the mixture is kept in the cold from 12 hr to 1 month. Electrophoresis (Beckman Paragon system for Hb) gives a new band. This new band gives a new band positive to benzidine staining. This methodology is applied for the reconstitution of the β-globin prepared from other FX globin fusion proteins and for the three variant Hbs which will be described below; it is highly reproducible. On the basis of densitometry scanning, it is estimated that from 1 liter of cell culture 5–15 mg of Hb can be reconstituted.

Example 4

Purification of the Native Modified Hemoglobin

The protein from Example 3 is equilibrated with 0.1 M glycine, pH 7.8, and absorbed on a DEAE cellulose column equilibrated with glycine 0.2M, pH 7.8. The modified Hb is separated from other contaminant protein, using a gradient elution of glycine 0.2 M, pH 7.8 and glycine 0.2 M and NaCl 0.06M, pH 7.8. The modified protein is collected as a single peak. In electrophoresis (Beckman Paragon) it gives only one single band.

Example 5

Two liters of Luri-Bertani (LB) Medium containing ampicillin (50 mg/l) is inoculated with 25 ml of an overnight culture of *E. coli* strain AR 120 which has been transformed with pJK05 (or an analogous plasmid bearing a mutant beta-globin gene), and grown at 37° C. until the optical absorbance at 650 nm reaches approximately 0.6. At that time, 2.0 ml of nalidixic acid solution (60 mg of nalidixic acid/ml of 1 M NaOH) is added and the bacteria allowed to continue growth for 20 hours. Isolation of the fusion protein, yield 100 mgs, cleavage with Factor $X_a$, and reconstitution with alpha chains is carried out as described in Examples 1 and 2 above. The yield of purified reconstituted hemoglobin tetramer is 20–40 mg per liter of culture.

Example 6

FIG. 9 shows the oxygen equilibrium curves of native Hb (control) (●), Hb reconstituted from recombinant β-chains (□), and the β-NA1(1) Val→meth, NA2(2) histidine deleted, HCl (144) Lys→Arg mutant Hb (Δ). These curves are obtained in 10 mM $P_1$, 100 mM NaCl, pH 7.4 at 25.5° C.

The values of P½ and Hill coefficients are listed in Table VI.

TABLE VI

| Protein | P½ | n |
|---|---|---|
| Hb natural | 1.91 | 2.6 |
| Hb reconstituted | 2.0 | 2.2 |
| Hb-βNA1(1) Val → meth, NA2(2) histidine deleted, HCl(144) Lys → Arg | 3.4 | 2.8 |

Example 7

Figure 11:
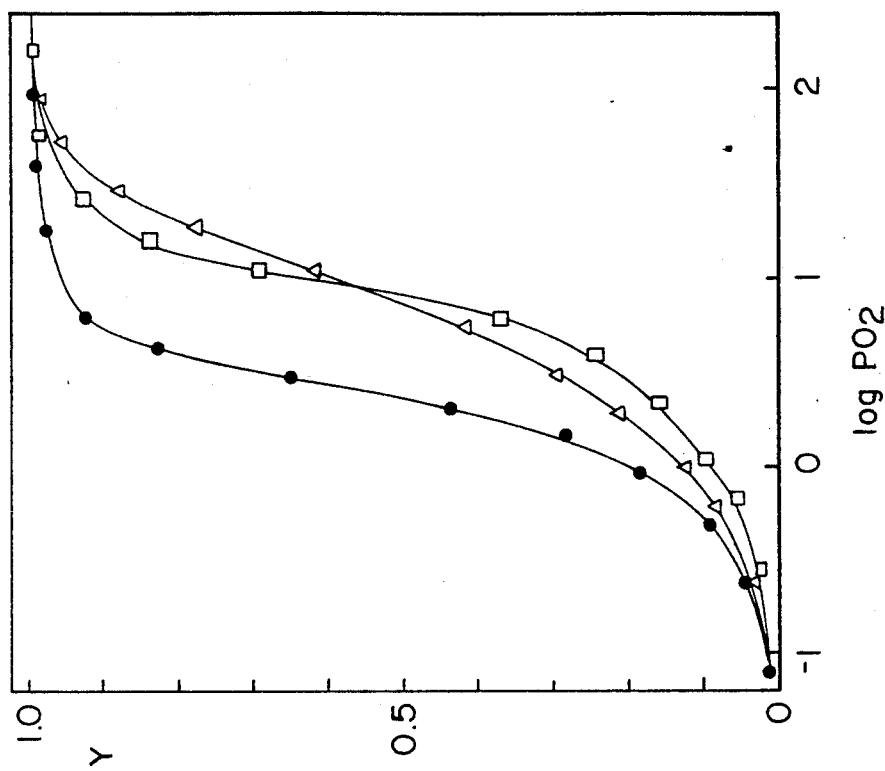

FIG. 11 shows the oxygen affinity of native Hb (control), of mutant βE11(67)Val→Thr (0), and of the mutant βA1(4) Thr→Asp. Val(67)E11β is one of the nearly invariant residues in all Hbs and myoglobins. Its substitution with a side chain of essentially the same size and shape but introducing a polar hydroxyl group into the pocket has the effect of decreasing the oxygen affinity. In the second mutant, the introduction of a negative charge close to the N-terminal end mimics the effect of 2,3-DPG and lowers the oxygen affinity.

Example 8

Figure 12:
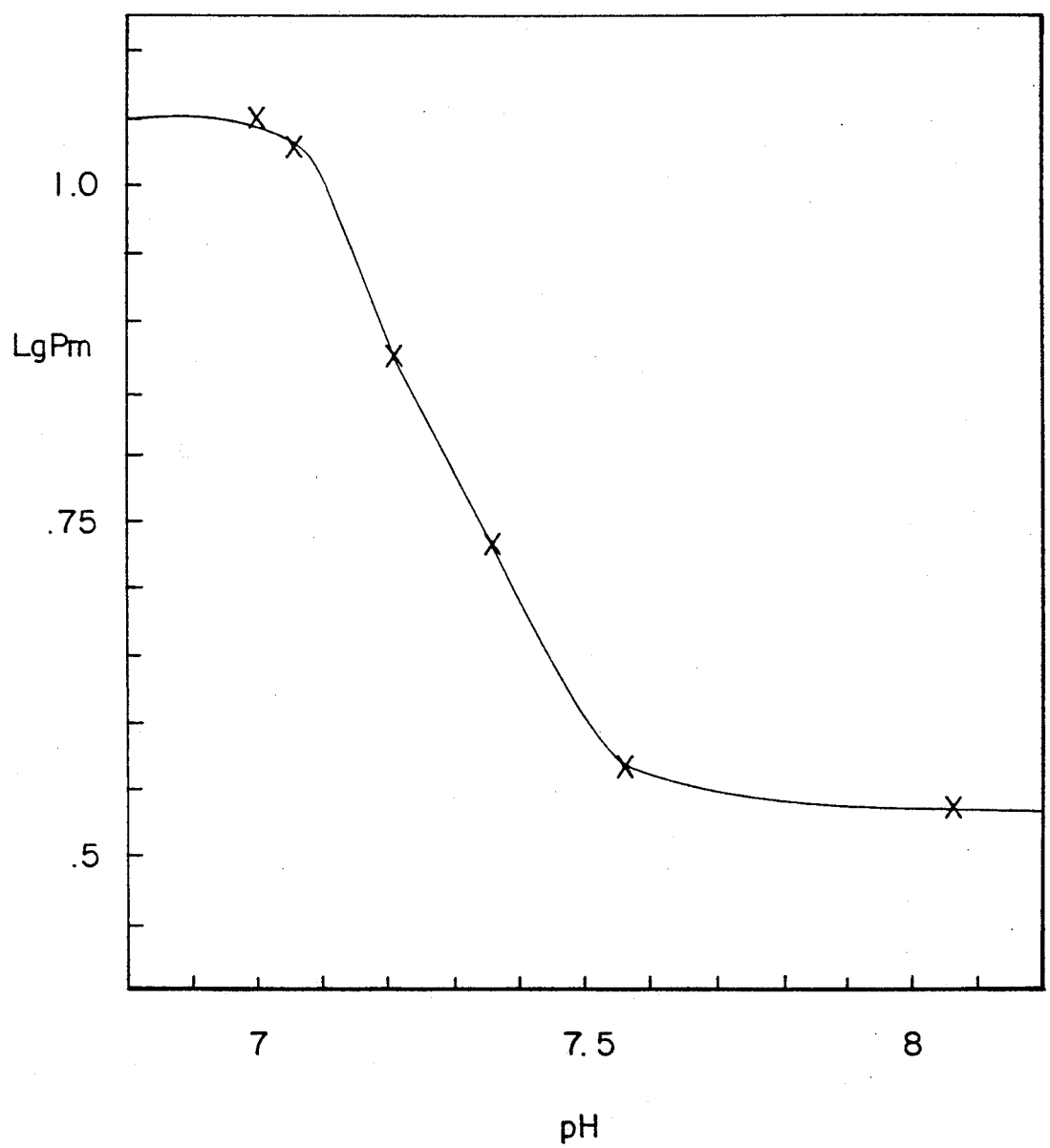

FIG. 12 represents the Bohr effect of Hb-βE11(67)Val→Thr. From the slope of the curve it can be calculated that one proton/heme is released upon oxygenation for a total of 4 proton/tetramer.

Table VII lists the functional characteristics measured for the modified Hb βE11(67) Val→Thr and for the modified Hb βA1 (4) Thr→Asp. A control of normal Hb is also included.

TABLE VI

Oxygen affinities on normal and recombinant mutant Hbs, measured at 25° Buffer: Phosphate 10 mM, NaCl 80 mM, Borax 100 mM.

| Protein | pH | $P_{50}$ | n |
|---|---|---|---|
| HbA (control) | 7.36 | 3.48 | 2.6 |
| Hb-βE11(67) Val → Thr | 7.00 | 12.7 | 1.1 |
|  | 7.06 | 11.6 | 1.2 |
|  | 7.21 | 7.51 | 1.5 |
|  | 7.26 | 6.8 | 1.6 |
|  | 7.36 | 5.6 | 1.1 |
|  | 7.56 | 4.15 | 1.1 |
|  | 8.06 | 3.84 | 1.7 |
| HbβA1(4) Thr → Asp | 7.36 | 11.5 | 2.35 |

Example 9

Design of Variant Human Hemoglobins

The objective is to introduce in human Hb specific amino acid substitutions which should confer on the protein an enhanced sensitivity toward $Cl^-$ ions so as to have low oxygen affinity and cooperative oxygen binding while making as few amino acid substitutions as possible. As a result, a different mechanism for oxygen affinity regulation will be obtained as an alternative to the more common regulation of oxygen affinity by organic phosphates, present in most vertebrates.

Example 10

The following site specific mutant is constructed:

βNA1(1)Val→Met; delete β-NA2(2)His

These changes produce an N-terminal end very similar to that of bovine Hb. The only difference in the first 8 residues is a proline at A2(5)β rather than an alanine at that position in bovine Hb.

Example 11

The following site specific mutant is constructed:

β-HCl(144)Lys→Arg

The presence of an arginine in position HClβ is a characteristic common to all ruminant β-chains, and may contribute to a Cl⁻ binding site. In the T conformation, a Cl⁻ binding site can be formed by the juxtaposition of the $\beta_1$ N-terminal amino group and the Arg-HCl$\beta_2$ guanidinium group. This site is structurally analogous to the Cl⁻ binding site in the salt bridge network between the two β-chains in deoxyHb.

Example 12

The following site specific mutant has been constructed:

βNA1(1) Val→Met; βNA2(2) His deleted;
βHCl(144)Lys→Arg

This is a combination of the above mutants of Examples 6 and 7. Convenient restriction sites exist so that a segment bearing the HCl substitution can be moved as a cassette. If Arg-Hclβ is involved in Cl⁻ binding in bovine Hb, this mutant should possess at least qualitative similarity to bovine Hb in respect to Cl⁻ regulation. This mutant is further described in Example 6.

Example 13

The following site specific mutant is constructed:

βNA1(1)Val→Met; βNA2(2)His deleted;
βE20O(76)Ala→Lys

This mutant has an N-terminal end similar to bovine Hb, plus the presence of a Lysine at E20β. According to our hypothesis, this mutant undergoes a decrease in oxygen affinity upon the addition of Cl⁻.

Example 14

The following site specific mutant is constructed:

β-NA1(1)Val→Met; β-NA2(2)His deleted;
βE20(76)Ala→Lys; βHCl (144) Lys→Arg

This mutant contains the two proposed Cl⁻ binding sites. They both might be relevant to the enhanced sensitivity to Cl⁻ ions found in bovine Hb.

Example 15

A mutant where only His-NA2β is deleted, producing an N-terminal sequence, Val-Leu-Thr..., is helpful in establishing whether the N-terminal methionine is essential for the modulation of Cl⁻ binding, or if its role can be filled by other hydrophobic side chains.

Example 16

A mutant where βA2(5) Pro is replaced with more flexible amino acids such as Gly or Ala.

Example 17

Substituting the amino acids at positions E13β, E14β and E19β with the respective residues present in the bovine β-globin, or any other amino acids with similar characteristics.

According to our hypothesis, these mutants provide Hbs representing various stages in the creation of conformationally sensitive Cl⁻ binding sites in human hemoglobin.

Example 18

One further group of mutants is illustrative of an approach to preventing dissociation of the hemoglobin tetramer into α-β dimers. The objective is to utilize a Cys-S-S-Cys to crosslink between like chains positioned such that it would be unlikely to cause a major perturbation of the allosteric equilibrium. A typical approach is the introduction of extension peptides at the amino or carboxyl end of the cloned gene for the β and β chains. Typical extension peptides would be NH2-cysteine (glycine) where the number of glycine residues determine the length of the peptide and the cysteines establish a new S-S intramolecular crosslink.

Example 19

Variants at β1

Substitution of valine (GUG) with a methionine (AUG) or a leucine (CUG) considerably alters the properties of the β1 amino-terminal end. Methionine is more hydrophilic than the original valine and has a larger side chain. Leucine, although it has an hydrophobicity very similar to that of valine, has an extra carbon atom in the side chain. These variants mimic the substitution present in Hb Raleigh.

Example 20

Variants at β2

Substitution of histidine (CAC) with either leucine (CUC), tyrosine (UAC) or aspartic acid (GAG). In all cases the substituting amino acids have different characteristics than the original histidine. Leucine is strongly hydrophobic, tyrosine has a phenolic ring which at neutral pH is uncharged while in normal Hb the imidazole ring of histidine can carry a positive charge. Both mutations increase the hydrophobicity of the β-aminoterminal residues and are expected to produce variant Hbs with decreased oxygen affinity. Aspartic acid is strongly hydrophilic and should increase the oxygen affinity. However, it will carry two negatively charged groups into the DPG pocket. In the reconstituted hemoglobin this would add a total of two negative charges per molecule of hemoglobin, simulating the effect of 2,3-DPG and decreasing the oxygen affinity.

Example 21

Variants at $\beta_1\beta_2$

Construct double variants from the plasmids carrying a mutation either at $\beta_1$ or at $\beta_2$. These variants can be combinations of the single amino acid mutations above described. In these mutants the $\beta_1\beta_2$ valine-histidine residues can be substituted by: methionine-leucine, methionine-aspartic acid, methionine-tyrosine, leucine-leucine, leucine-aspartic acid, leucine-tyrosine. These mutants can be used to investigate the effect of the combination of the two amino acid mutations on the functional properties of Hb.

All references cited herein including U.S. patent applications are herein incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A purified hemoglobin protein comprising a polypeptide having the amino acid sequence of the normal human hemoglobin β-chain modified by the mutation of residue βE11(67) from valine to threonine, said protein having a decreased oxygen binding affinity compared to normal human hemoglobin which results from a higher affinity for chloride ion in said modified β-chain compared to normal human hemoglobin.

2. A purified hemoglobin protein comprising a polypeptide having the amino acid sequence of the normal human hemoglobin β-chain modified by the mutation of residue βNA1(1) from valine to methionine, the deletion of the histidine residue NA2(2) and mutation of the residue HCl(144) from lysine to arginine, as set forth in FIG. 14, said protein having an additional binding site for chloride ion and a lower oxygen affinity compared to normal human hemoglobin.

3. A purified hemoglobin protein comprising a polypeptide having the amino acid sequence of normal human hemoglobin β-chain modified by the mutation of residue βNA(1) from valine to methionine, the deletion of the histidine residue NA(2) and mutation of residue E20(76) from alanine to lysine, said protein having an additional binding site for chloride ion and a lower oxygen affinity compared to normal human hemoglobin.

4. A purified hemoglobin protein comprising a polypeptide having the amino acid sequence of normal human hemoglobin β-chain modified by the mutation of residue βNA(1) from valine to methionine, the deletion of the histidine residue NA(2), mutation of residue E20(76) from alanine to lysine and mutation of the residue HCl(144) from lysine to arginine, said protein having an additional binding side for chloride ion and a lower oxygen affinity compared to normal human hemoglobin.

5. A purified hemoglobin protein comprising a polypeptide having the amino acid sequence of normal human hemoglobin β-chain modified by the mutation of residue A2(5) from proline to alanine, said protein having an additional binding site for chloride ion and a lower oxygen affinity compared to normal human hemoglobin.

* * * * *